United States Patent
Berst et al.

(10) Patent No.: US 12,258,680 B2
(45) Date of Patent: Mar. 25, 2025

(54) SOLID SUPPORT

(71) Applicant: NOVARTIS AG, Basel (CH)

(72) Inventors: Frederic Berst, Altkirch (FR); Yves Ruff, Strasbourg (FR)

(73) Assignee: NOVARTIS AG, Basel (CH)

( * ) Notice: Subject to any disclaimer, the term of this patent is extended or adjusted under 35 U.S.C. 154(b) by 1125 days.

(21) Appl. No.: 17/055,733

(22) PCT Filed: May 17, 2019

(86) PCT No.: PCT/IB2019/054094
§ 371 (c)(1),
(2) Date: Nov. 16, 2020

(87) PCT Pub. No.: WO2019/220406
PCT Pub. Date: Nov. 21, 2019

(65) Prior Publication Data
US 2021/0207288 A1 Jul. 8, 2021

(30) Foreign Application Priority Data

May 18, 2018 (EP) .................... 18173182

(51) Int. Cl.
*C40B 50/14* (2006.01)
*C07C 237/12* (2006.01)
*G01N 33/545* (2006.01)

(52) U.S. Cl.
CPC ............ *C40B 50/14* (2013.01); *C07C 237/12* (2013.01); *G01N 33/545* (2013.01); *C07B 2200/11* (2013.01); *C07C 2601/14* (2017.05)

(58) Field of Classification Search
None
See application file for complete search history.

(56) References Cited

U.S. PATENT DOCUMENTS

| 2012/0115751 A1 | 5/2012 | Winssinger et al. |
| 2015/0209440 A1 | 7/2015 | Eliasof et al. |

OTHER PUBLICATIONS

Nisha et al., "Complexes of Poly(ethylene glycol)-Based Cationic Random Copolymer and Calf Thymus DNA: A Complete Biophysical Characterization," Langmuir 2004, 20:2386-2396. (Year: 2004).*
Antunes et al., "Effect of replacing main-chain ureas with thiourea and guanidinium surrogates on the bactericidal activity of membrane active oligourea foldamers," Bioorg. Med. Chem. 2017, 25:4245-4252. (Year: 2017).*
Nisha et al: "Complexes of Poly(ethylene glycol)-Based Cationic Random Copolymer and Calf Thymus DNA: A Complete Biophysical Characterization", Langmuir, (2004), 20(6):2386-2396.
Katayose et al: "Water-Soluble Polyion Complex Associates of DNA and Poly(Ethylene Glycol)-Poly(L-Lysine) Block Copolymer", Bioconjugate Chemistry, (1997), 8(5):702-707.
Fenske et al: Cationic Poly(ethyleneglycol) Lipids Incorporated into Pre-formed vesicles Enhance Binding and Uptake to BHK cells, Biochimica ET Biophysica Acta (BBA)—Biomembranes, Elsevier, Amsterdam, NL, (2001), 1512 (2):259-272.

(Continued)

*Primary Examiner* — Kaijiang Zhang
(74) *Attorney, Agent, or Firm* — Emily T. Wu

(57) ABSTRACT

A solid support for use in non-aqueous DNA-conjugated molecule reactions, wherein the support comprises a solid body formed from a plurality of polyethylene glycol units, wherein the solid body includes at least one cationic moiety.

13 Claims, 1 Drawing Sheet
Specification includes a Sequence Listing.

(56) References Cited

OTHER PUBLICATIONS

MacConnell et al: "An Integrated Microfluidic Processor for DNA-Encoded Combinatorial Library Functional Screening", ACS Combinatorial Science, (2017), 19(3):181-192.

Walsh et al: "Optimizing the immobilization of single-stranded DNA onto glass beads", Journal of Biochemical and Biophysical Methods, Amsterdam, NL, (2001), 47:221-231.

Tada et al, "PEGylated Antibodies and DNA in Organic Media and Genetic PEGylation" In: "ACS Symposium Series", Jan. 1, 2013, American Chemistry Society/Oxford University Press, vol. 1144, pp. 223-233.

Annunziata at al, "A Poly(ethylene glycol)-Supported Quaternary Ammonium Salt:? An Efficient, Recoverable, and Recyclable Phase-Transfer Catalyst", Organic Letters, (2000), 2(12):1737-1739.

Du et al, "Quaternary Ammonium Bromide Functionalized Polyethylene Glycol: A Highly Efficient and Recyclable Catalyst for Selective Synthesis of 5-Aryl-2-oxazolidinones from Carbon Dioxide and Aziridines Under Solvent-Free Conditions", Journal of Organic Chemistry, (2008), 73(12):4709-4712.

Lv et al, "Catalytic asymmetric epoxidation of chalcones under poly(ethylene glycol)-supported Cinchona ammonium salt catalyzed conditions", "Tetrahedron: Asymmetry", Pergamon Press Ltd, Oxford, GB, (2006), 17(3):330-335.

Wang et al, "Cationic nanoparticles with quaternary ammonium-functionalized PLGA-PEG-based copolymers for potent gene transfection", Journal of Nanoparticle Research, (2013), 15(11).

Vinogradov et al., "Self-assembly of polyamine-poly(ethylene glycol) copolymers with phosphorothioate oligonucleotides", Bioconjugate Chemistry, Americal Chemical Society, US, (1998), 9(6):805-812.

Pon, "Solid-Phase Supports for Oligonucleotides Synthesis" In: "Current Protocols in Nucleic Acid Chemistry", 2000, John Wiley & Sons, Inc., Hoboken, NJ, USA.

Halpin D R et al: "DNA Display III. Solid-Phase Organic Synthesis on Unprotected DNA", Plos Biology, Public Library of Science, US, (2004), 2(7):1031-1038.

Škopic M K et all "Acid- and Au(I)-mediated synthesis of hexathymidine-DNAheterocycle chimeras, an efficient entry to DNA-encoded libraries inspired by drug structures", Chemical Science, (2017), 5(8):3356-3361.

* cited by examiner

Figure 1: TentaGel (RTM) XV-NH₂ resin of Formula (VI)
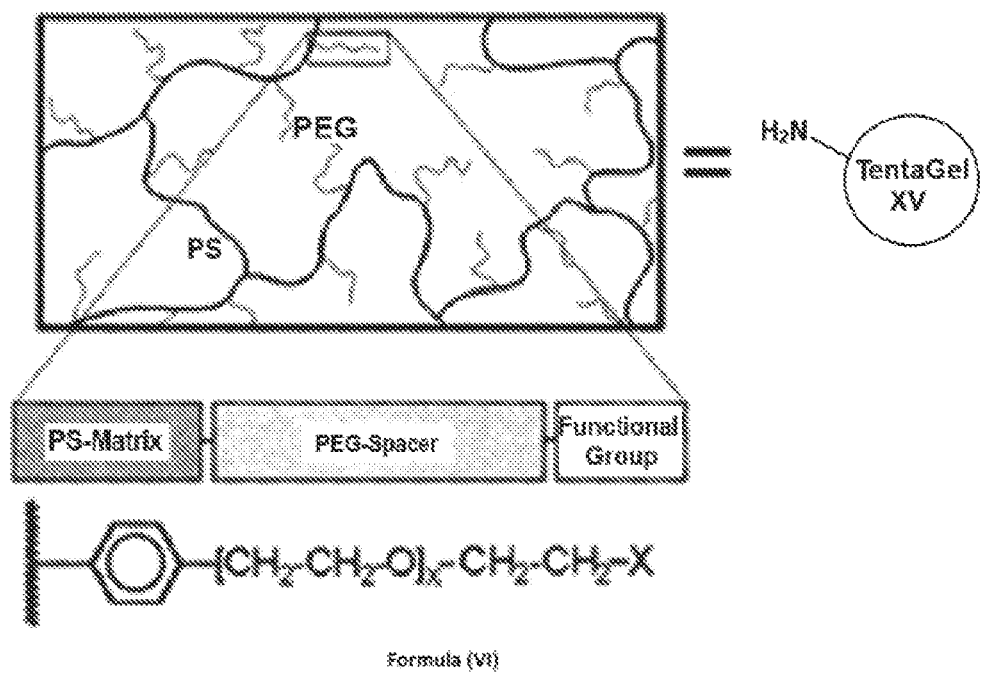
Figure 2: Cationic amphiphilic solid support
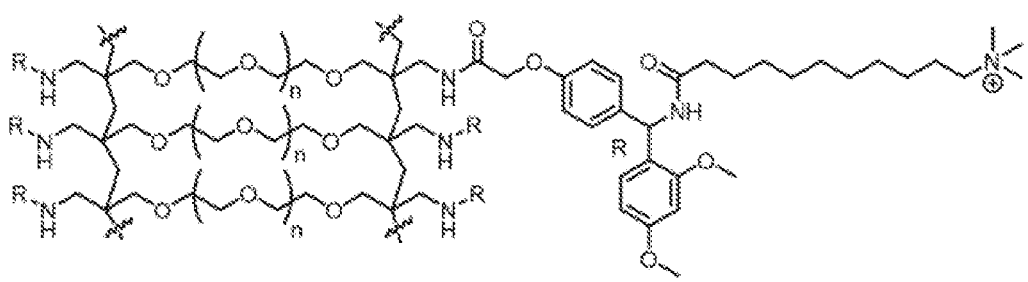
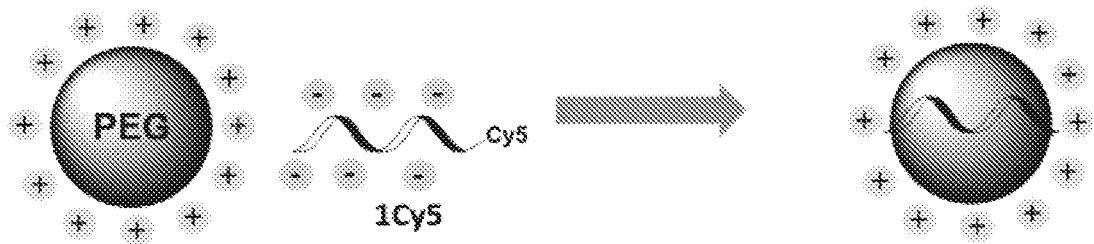

SOLID SUPPORT

SEQUENCE LISTING

The instant application contains a Sequence Listing which has been submitted electronically in ASCII format and is hereby incorporated by reference in its entirety. Said ASCII copy, created on Nov. 4, 2020, is named PAT058142-US-PCT-Sequence_Listing.txt and is 355 bytes in size.

FIELD OF THE INVENTION

The present invention relates to solid supports, which are suitable for use in non-aqueous chemical reactions, for example in chemical reactions conducted on DNA or in the presence of DNA to synthesize DNA-encoded libraries (DELs), and also to a method of using these solid supports, which method includes the steps of adsorbing the DNA onto the solid support of the invention and reacting the DNA-labelled compound with a reagent in a non-aqueous solvent system.

BACKGROUND OF THE INVENTION

DNA Encoded Libraries (DELs) are collections of hundreds of thousands to billions of synthetic small molecules each conjugated to a unique DNA sequence serving as a structural identifier. These vast collections of synthetic small molecule-DNA conjugates are screened in mixtures by affinity selection processes, making them an attractive tool for the discovery of ligands to biomolecular targets of pharmaceutical interest. Reactions leveraged for the synthesis of DELs typically involve the formation of covalent chemical bonds under mild aqueous conditions that are compatible with the solubility and stability of the nucleic acid tags or labels. The solubilization of nucleic acids typically requires a high proportion of water, which has the inevitable consequence of inducing side reactions, like protonation of reagents or reaction intermediates or reagent hydrolysis in reactions used for DELs synthesis. This severely limits the implementation of novel chemical transformations for DEL synthesis and these are typically restricted to those that have the potential to work in the presence of water. Many of these reactions are nitrogen-derivatization chemistries (such as amidation, reductive amination, sulfonylation, urethanation) or palladium-mediated cross couplings (and most prominently the Suzuki cross-coupling), which can lead to molecules with limited drug-like properties that may require significant optimization to deliver clinical candidates.

It is known to immobilize DNA-conjugated molecules onto a solid support in order to increase the proportion of organic solvent that is used in the reactions. The typical support in such cases is a polysaccharide support, such as DEAE sepharose. However, such polysaccharide solid supports are hydrophilic and are thus practically impossible to dry thoroughly. In addition, such solid-supports are not compatible with all the organic solvents typically used in organic synthesis.

Currently, methods to carry out reactions on DNA-conjugated small molecules in organic solvents with total exclusion of water are limited to covalent attachment of the DNA molecule to a solid support (MacConnell A. B., Price A. K. & Paegel B. M. An integrated microfluidic processor for DNA-encoded combinatorial library functional screening. ACS Combinatorial Science, 2017(3), 181-192; Klika Škopić M., Salamon H., Bugain O., Jung K., Gohla A., Doetsch L. J., Dos Santos D., Bhat A., Wagner B., Brunschweiger A. Acid- and Au(I)-mediated synthesis of hexathymidine-DNA-heterocycle chimeras, an efficient entry to DNA-encoded libraries inspired by drug structures. *Chemical Science,* 2017(8), 3356-3361). In these examples, the covalent attachment of the DNA to the solid support either prevents screening the library against immobilized target in affinity selection experiments, or prevents the elongation of the DNA tag to encode the structure of the library compounds. Adapting such transformations towards large, diverse library syntheses in aqueous environments remains a significant and costly challenge. Importantly, this strategy does not allow to immediately tap into advancements in modern organic chemistry that may be incompatible with the presence of water in DNA-compatible reaction media.

Therefore, there are currently no generic, practical methods for carrying out reactions on DNA-bound molecules in anhydrous organic solvents for the purpose of DNA encoded library synthesis.

The problem has been overcome through non-covalent adsorption of DNA-linked scaffolds by means of reversible ionic interactions on a PEG-based insoluble cationic support, which essentially makes it possible to conduct chemistry in the absence of water, and release from the support enables the miniaturization of DEL technology.

SUMMARY OF THE INVENTION

According to a first aspect of the invention, there is provided a solid support for use in non-aqueous DNA-conjugated molecule reactions, wherein the support comprises a solid body formed from a plurality of polyethylene glycol units, wherein the solid body includes at least one cationic moiety.

In a second aspect of the invention, there is provided a method of reacting a DNA-conjugated compound using one or more non-aqueous solvents, wherein the method includes the steps of adsorbing the DNA-labelled compound onto a solid support of the present invention and reacting the supported DNA-labelled compound with a reagent in a non-aqueous solvent system.

In a third aspect of the invention, there is provided the use of a solid support according to the present invention to support a DNA-conjugated compound.

DESCRIPTION OF THE DRAWINGS

FIG. 1. Pegylated solid polymeric TentaGel® XV—NH$_2$ resin having the formula (VI).

FIG. 2. Chemical Structure and schematic representation of an amphiphilic polymeric support of the present invention and its use in the transfer and immobilization of a DNA oligonucleotide, here conjugated to a Cy5 dye.

DETAILED DESCRIPTION OF THE INVENTION

The polyethylene glycol based solid resins (PEG-based resins) have been found to be suitable for use in the desired reactions, as they can be used under both aqueous and organic conditions. The solid supports include the amphiphilic properties of the PEG-based resin and a nucleic acid binding capability provided by the cationic moiety. The cationic moiety provides reversible electrostatic interactions with the nucleic acids. Thus, the solid support according to the invention can be suspended in water for DNA adsorption and then washed with organic solvents to leave the immobilized DNA encoded molecules under pseudo organic conditions. The solid supports according to the invention may thus be used in non-aqueous chemical transformations involving DNA-conjugated molecules, which solid supports are insoluble in both aqueous and organic solvent systems and furthermore, inert.

Advantageously, it is possible to substantially eliminate water from the support system via the use of known drying methods, such as the addition of molecular sieves.

The dried immobilized DNA encoded molecules can undergo non-aqueous reactions that were not previously possible.

In an embodiment of the invention, the cationic moiety includes a quaternary ammonium group or a guanidinium group.

For example, the cationic moiety may be a compound according to Formula I, Formula II or Formula III as defined below, (I) A compound according to Formula I:

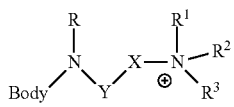

Formula I wherein:
Body is the solid support formed from a plurality of polyethylene glycol units;
R is hydrogen; $C_1$-$C_8$ alkyl optionally substituted by hydroxy, phenyl, $C_3$-$C_8$ cycloalkyl, 5 to 10 membered heterocyclic ring or —$OC_1$-$C_8$ alkyl; $C_3$-$C_8$ cycloalkyl; —$C(O)C_1$-$C_8$ alkyl; or a 5 to 10 membered heterocyclic ring;
X is $X_1$ or $X_2$, wherein
$X_1$ is a $C_1$-$C_{20}$ alkylene chain, wherein the chain is straight or branched and is optionally substituted by one or more substituents selected from halogen, —OH, $C_1$-$C_8$ alkoxy, nitro, cyano, —COOH, carbamoyl, —$N(R^4)R^5$, $C_3$-$C_6$ cycloalkyl, 3 to 7 membered heterocyclic ring, phenyl, 5 or 6 membered heteroaryl, or $C_1$-$C_4$ alkyl-phenyl; a $C_2$-$C_{20}$ alkenylene chain, wherein the chain is straight or branched, contains one or more carbon-carbon double bonds and is optionally substituted by one or more substituents selected from halogen, —OH, $C_1$-$C_8$ alkoxy, nitro, cyano, —COOH, carbamoyl, —$N(R^4)R^5$, $C_3$-$C_6$ cycloalkyl, 3 to 7 membered heterocyclic ring, phenyl, 5 or 6 membered heteroaryl, or $C_1$-$C_4$ alkyl-phenyl; or a $C_2$-$C_{20}$ alkynylene chain, wherein the chain is straight or branched, contains one or more carbon-carbon triple bonds and is optionally substituted by one or more substituents selected from halogen, —OH, $C_1$-$C_8$ alkoxy, nitro, cyano, —COOH, carbamoyl, —$N(R^4)R^5$, $C_3$-$C_6$ cycloalkyl, 3 to 7 membered heterocyclic ring, phenyl, 5 or 6 membered heteroaryl, or $C_1$-$C_4$ alkyl-phenyl;
$X_2$ is —Z—$X_1$—
wherein Z is selected from —$(CH_2)_a$—$R_x$—$(CH_2)_a$—NH—C(=O)—; —$(CH_2)_a$—CH(($CH_2)_a$—$R_{x1}$)NH—C(=O)—; —$(CH_2)_a$—$(O)_{0-1}$—$R_{x2}$—$CH(R_{x3})NH$—C(=O)—; and —$(CH_2)_b$—$(O)_{0-1}$—$(CH_2)_b$—NH—C(=O)—;
a is an integer from 0 to 6;
b is an integer from 1 to 6;
$R_x$ is selected from phenyl; $C_3$-$C_8$ cycloalkylene; —$C(H)_{2-x}((C_1$-$C_6$alkyl)_x)$-; naphthyl; and anthracyl, which phenyl, $C_3$-$C_8$ cycloalkylene, $C_1$-$C_6$alkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x1}$ is selected from phenyl; $C_3$-$C_8$ cycloalkyl; naphthyl; and anthracyl, which phenyl, $C_3$-$C_8$ cycloalkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x2}$ is selected from phenyl; $C_3$-$C_8$ cycloalkylene; naphthyl; and anthracyl, which phenyl, $C_3$-$C_8$ cycloalkylene, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x3}$ is selected from hydrogen; phenyl; and $C_3$-$C_6$cycloalkyl, which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;
x is an integer from 0 to 2;
Y is C(O) or $CH_2$; and
$R^1$, $R^2$, $R^3$, $R^4$ and $R^5$ are each independently selected from hydrogen; hydroxy; $C_1$-$C_8$ alkyl optionally substituted by hydroxy, phenyl, $C_3$-$C_8$ cycloalkyl, 5 to 10 membered heterocyclic ring or —$OC_1$-$C_8$ alkyl; $C_3$-$C_8$ cycloalkyl; —$C(O)C_1$-$C_8$ alkyl; or a 5 to 10 membered heterocyclic ring; or (II) A compound according to Formula II:

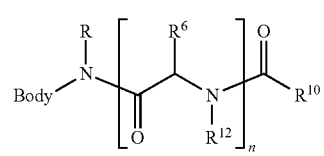

Formula II wherein:
Body is as defined above;
R is as defined above;
$R^{10}$ is a $C_1$-$C_8$ alkyl optionally substituted by hydroxy, phenyl, $C_3$-$C_8$ cycloalkyl, 5 to 10 membered heterocyclic ring or —$OC_1$-$C_8$ alkyl; $C_3$-$C_8$ cycloalkyl; a 5 to 10 membered heterocyclic ring or $R^{11}$;
n is an integer from 2 to 12;
$R^{12}$ is hydrogen; $C_1$-$C_8$ alkyl optionally substituted by hydroxy, phenyl, $C_3$-$C_8$ cycloalkyl, 5 to 10 membered heterocyclic ring or —$OC_1$-$C_8$ alkyl; $C_3$-$C_8$ cycloalkyl; —$C(O)C_1$-$C_8$ alkyl; or a 5 to 10 membered heterocyclic ring; and
$R^6$ and $R^{11}$ are each independently selected from:
(a) a group having the formula IIa:

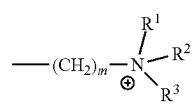

Formula IIa wherein m is an integer from 0 to 8; and
$R^1$, $R^2$ and $R^3$ are as defined above;

OR (b) a group having the formula IIb:

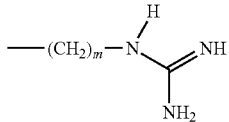

Formula IIb wherein m is as defined above;

OR (c) a group having the formula —$(CH_2)_q$—$NHR^7$
wherein q is an integer from 1 to 6; and
$R^7$ is a group having the formula IIc:

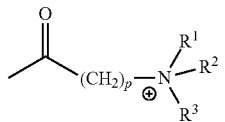

Formula IIc wherein p is an integer from 1 to 12; and
$R^1$, $R^2$ and $R^3$ are as defined above; or (III) A compound according to Formula III:

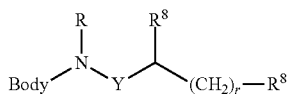

Formula III wherein
Body is as defined above;
R is as defined above;
Y is as defined above;
r is an integer from 1 to 6; and
$R^8$ is a group having the formula IIIa

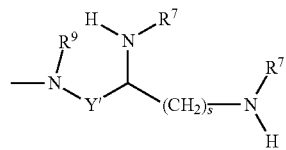

wherein
Y' is C(O) or $CH_2$;
s is an integer from 1 to 6;
$R^7$ is as defined above; and
$R^9$ is H or $C_1$-$C_6$ alkyl;

OR $R^8$ is a group having the formula IIIb

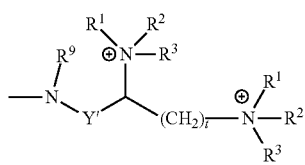

wherein
Y' is as defined above;
t is an integer from 1 to 6; and
$R^1$, $R^2$, $R^3$ and $R^9$ are as defined above.

In an embodiment of the invention, R and $R^{12}$ are each independently hydrogen or $C_1$-$C_6$ alkyl, suitably R and $R^{12}$ are each independently hydrogen.

In a further embodiment of the invention, $R^1$, $R^2$ and $R^3$ are the same. Suitably, $R^1$, $R^2$ and $R^3$ are each independently a $C_1$-$C_6$ alkyl. In a yet further embodiment of the invention, $R^1$, $R^2$ and $R^3$ are each methyl.

In a further embodiment of the invention, $R^4$ and $R^5$ are each independently selected from hydrogen and a $C_1$-$C_6$ alkyl.

In a further embodiment of the invention, $R^9$ is hydrogen.

In a further embodiment, $R^{10}$ is a $C_1$-$C_8$ alkyl, optionally a $C_1$-$C_3$ alkyl, further optionally a methyl group.

In a further embodiment, $X_1$ is a $C_1$-$C_{20}$ alkylene chain, which alkylene chain is straight and unsubstituted.

In a further embodiment, $X_1$ is a $C_1$-$C_{10}$ alkylene chain, which alkylene chain is straight and unsubstituted.

In a further embodiment of the invention, the cationic moiety is a compound of formula (I),
wherein
X is $X_1$ or $X_2$, wherein
$X_1$ is a $C_1$-$C_{20}$ alkylene chain, wherein the chain is straight or branched and is optionally substituted by one or more substituents selected from halogen, —OH, $C_1$-$C_8$ alkoxy, nitro, cyano, —COOH, carbamoyl, —$N(R^4)R^5$, $C_3$-$C_6$ cycloalkyl, 3 to 7 membered heterocyclic ring, phenyl, 5 or 6 membered heteroaryl, or $C_1$-$C_4$ alkyl-phenyl;
$X_2$ is —Z—$X_1$—
wherein Z is selected from —$(CH_2)_a$—$R_x$—$(CH_2)_a$—NH—C(=O)—; —$(CH_2)_a$—CH(($CH_2)_a$—$R_{x1}$)NH—C(=O)—; —$(CH_2)_a$—$(O)_{0-1}$—$R_{x2}$—CH($R_{x3}$)NH—C(=O)—; and —$(CH_2)_b$—$(O)_{0-1}$—$(CH_2)_b$—NH—C(=O)—;
a is an integer from 0 to 6;
b is an integer from 1 to 6;
$R_x$ is selected from phenyl; $C_3$-$C_8$ cycloalkylene; —C(H)$_{2-x}$(($C_1$-$C_6$alkyl)$_x$)-; naphthyl; and anthracyl,
which phenyl, $C_3$-$C_8$ cycloalkylene, $C_1$-$C_6$alkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x1}$ is selected from phenyl; $C_3$-$C_8$ cycloalkyl; naphthyl; and anthracyl,
which phenyl, $C_3$-$C_8$ cycloalkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x2}$ is selected from phenyl; $C_3$-$C_8$ cycloalkylene; naphthyl; and anthracyl,
which phenyl, $C_3$-$C_8$ cycloalkylene, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x3}$ is selected from hydrogen; phenyl; and $C_3$-$C_6$cycloalkyl,
which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;
x is an integer from 0 to 2.

In a further embodiment, the cationic moiety is a compound of formula (I), wherein R is hydrogen;
Y is C(O);
X is $X_1$ or $X_2$, wherein
$X_1$ is a $C_1$-$C_{20}$ alkylene chain, wherein the chain is straight or branched and is optionally substituted by one or more substituents selected from halogen, —OH, $C_1$-$C_8$ alkoxy, nitro, cyano, —COOH, carbamoyl, —N($R^4$)$R^5$, $C_3$-$C_6$ cycloalkyl, 3 to 7 membered heterocyclic ring, phenyl, 5 or 6 membered heteroaryl, or $C_1$-$C_4$ alkyl-phenyl;
$X_2$ is —Z—$X_1$—
wherein Z is selected from —$(CH_2)_a$—$R_x$—$(CH_2)_a$—NH—C(=O)—; —$(CH_2)_a$—CH(($CH_2)_a$—$R_{x1}$)NH—C(=O)—; —$(CH_2)_a$—$(O)_{0-1}$—$R_{x2}$—CH($R_{x3}$)NH—C(=O)—; and —$(CH_2)_b$—$(O)_{0-1}$—$(CH_2)_b$—NH—C(=O)—;
a is an integer from 0 to 6;
b is an integer from 1 to 6;
$R_x$ is selected from phenyl; $C_3$-$C_8$ cycloalkylene; —C(H)$_{2-x}$(($C_1$-$C_6$alkyl)$_x$)-; naphthyl; and anthracyl,
which phenyl, $C_3$-$C_8$ cycloalkylene, $C_1$-$C_6$alkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x1}$ is selected from phenyl; $C_3$-$C_8$ cycloalkyl; naphthyl; and anthracyl,
which phenyl, $C_3$-$C_8$ cycloalkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x2}$ is selected from phenyl; $C_3$-$C_8$ cycloalkylene; naphthyl; and anthracyl,
which phenyl, $C_3$-$C_8$ cycloalkylene, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x3}$ is selected from hydrogen; phenyl; and $C_3$-$C_6$cycloalkyl,
which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;
x is an integer from 0 to 2;
$R^1$, $R^2$ and $R^3$ are each independently selected from hydrogen; hydroxy; $C_1$-$C_8$ alkyl optionally substituted by hydroxy, phenyl, $C_3$-$C_8$ cycloalkyl, 5 to 10 membered heterocyclic ring or —$OC_1$-$C_8$ alkyl; $C_3$-$C_8$ cycloalkyl; —C(O)$C_1$-$C_8$ alkyl; or a 5 to 10 membered heterocyclic ring.

In a further embodiment, the cationic moiety is a compound of formula (I), wherein R is hydrogen;
Y is C(O);
X is $X_1$ or $X_2$, wherein
$X_1$ is a $C_1$-$C_{20}$ alkylene chain, wherein the chain is straight or branched;
$X_2$ is —Z—$X_1$—
wherein Z is selected from —$(CH_2)_a$—$R_x$—$(CH_2)_a$—NH—C(=O)—; —$(CH_2)_a$—CH(($CH_2)_a$—$R_{x1}$)NH—C(=O)—; —$(CH_2)_a$—$(O)_{0-1}$—$R_{x2}$—CH($R_{x3}$)NH—C(=O)—; and —$(CH_2)_b$—$(O)_{0-1}$—$(CH_2)_b$—NH—C(=O)—;
a is an integer from 0 to 6;
b is an integer from 1 to 6;
$R_x$ is selected from phenyl; $C_3$-$C_8$ cycloalkylene; —C(H)$_{2-x}$(($C_1$-$C_6$alkyl)$_x$)-; naphthyl; and anthracyl,
which phenyl, $C_3$-$C_8$ cycloalkylene, $C_1$-$C_6$alkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x1}$ is selected from phenyl; $C_3$-$C_8$ cycloalkyl; naphthyl; and anthracyl,
which phenyl, $C_3$-$C_8$ cycloalkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x2}$ is selected from phenyl; $C_3$-$C_8$ cycloalkylene; naphthyl; and anthracyl,
which phenyl, $C_3$-$C_8$ cycloalkylene, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x3}$ is selected from hydrogen; phenyl; and $C_3$-$C_6$cycloalkyl,
which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;
x is an integer from 0 to 2;

$R^1$, $R^2$ and $R^3$ are each independently selected from hydrogen; $C_1$-$C_8$ alkyl optionally substituted by phenyl, or $C_3$-$C_8$ cycloalkyl; $C_3$-$C_8$ cycloalkyl.

In a further embodiment, the cationic moiety is a compound of formula (I), wherein R is hydrogen;
Y is C(O);
X is $X_1$ or $X_2$, wherein
$X_1$ is a $C_1$-$C_{20}$ alkylene chain, wherein the chain is straight or branched and is optionally substituted by one or more substituents selected from halogen, —OH, $C_1$-$C_8$ alkoxy, nitro, cyano, —COOH, carbamoyl, —N($R^4$)$R^5$, $C_3$-$C_6$ cycloalkyl, 3 to 7 membered heterocyclic ring, phenyl, 5 or 6 membered heteroaryl, or $C_1$-$C_4$ alkyl-phenyl;
$X_2$ is —Z—$X_1$—
wherein Z is selected from —$(CH_2)_a$—$R_x$—$(CH_2)_a$—NH—C(=O)—; —$(CH_2)_a$—CH(($CH_2)_a$—$R_{x1}$)NH—C(=O)—; —$(CH_2)_a$—$(O)_{0-1}$—$R_{x2}$—CH($R_{x3}$)NH—C(=O)—; and —$(CH_2)_b$—$(O)_{0-1}$—$(CH_2)_b$—NH—C(=O)—;
a is an integer from 0 to 6;
b is an integer from 1 to 6;
$R_x$ is selected from phenyl; $C_3$-$C_8$ cycloalkylene; —C(H)$_{2-x}$(($C_1$-$C_8$alkyl)$_x$)-; naphthyl; and anthracyl,
which phenyl, $C_3$-$C_8$ cycloalkylene, $C_1$-$C_6$alkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x1}$ is selected from phenyl; $C_3$-$C_8$ cycloalkyl; naphthyl; and anthracyl,
which phenyl, $C_3$-$C_8$ cycloalkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x2}$ is selected from phenyl; $C_3$-$C_8$ cycloalkylene; naphthyl; and anthracyl,
which phenyl, $C_3$-$C_8$ cycloalkylene, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x3}$ is selected from hydrogen; phenyl; and $C_3$-$C_6$cycloalkyl,
which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;
x is an integer from 0 to 2;
$R^1$, $R^2$ and $R^3$ are each independently a $C_1$-$C_6$ alkyl, preferably $R^1$, $R^2$ and $R^3$ are each methyl.

In a further embodiment, the cationic moiety is a compound of formula (I), wherein R is hydrogen;
Y is C(O);
X is $X_1$ or $X_2$, wherein
$X_1$ is a $C_1$-$C_{20}$ alkylene chain, wherein the chain is straight or branched;
$X_2$ is —Z—$X_1$—
wherein Z is selected from —$(CH_2)_a$—$R_x$—$(CH_2)_a$—NH—C(=O)—; —$(CH_2)_a$—CH(($CH_2)_a$—$R_{x1}$)NH—C(=O)—; —$(CH_2)_a$—$(O)_{0-1}$—$R_{x2}$—CH($R_{x3}$)NH—C(=O)—; and —$(CH_2)_b$—$(O)_{0-1}$—$(CH_2)_b$—NH—C(=O)—;
a is an integer from 0 to 6;
b is an integer from 1 to 6;
$R_x$ is selected from phenyl; $C_3$-$C_8$ cycloalkylene; —C(H)$_{2-x}$(($C_1$-$C_6$alkyl)$_x$)-; naphthyl; and anthracyl,
which phenyl, $C_3$-$C_8$ cycloalkylene, $C_1$-$C_6$alkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x1}$ is selected from phenyl; $C_3$-$C_8$ cycloalkyl; naphthyl; and anthracyl,
which phenyl, $C_3$-$C_8$ cycloalkyl, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x2}$ is selected from phenyl; $C_3$-$C_8$ cycloalkylene; naphthyl; and anthracyl,
which phenyl, $C_3$-$C_8$ cycloalkylene, naphthyl or anthracyl are optionally substituted 1, 2, 3 or 4 times independently with $C_1$-$C_6$alkyl, $C_1$-$C_6$alkoxy, $C_1$-$C_6$ haloalkyl or halo;
$R_{x3}$ is selected from hydrogen; phenyl; and $C_3$-$C_6$cycloalkyl,
which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;
x is an integer from 0 to 2;
$R^1$, $R^2$ and $R^3$ are each independently a $C_1$-$C_6$ alkyl, preferably $R^1$, $R^2$ and $R^3$ are each methyl.

In a further embodiment, the cationic moiety is a compound of formula (I), wherein R is hydrogen;
Y is C(O);
X is $X_1$ or $X_2$, wherein
$X_1$ is a $C_1$-$C_{20}$ alkylene chain, wherein the chain is straight or branched and is optionally substituted by one or more substituents selected from halogen, —OH, $C_1$-$C_8$ alkoxy, nitro, cyano, —COOH, carbamoyl, —N($R^4$)$R^5$, $C_3$-$C_6$ cycloalkyl, 3 to 7 membered heterocyclic ring, phenyl, 5 or 6 membered heteroaryl, or $C_1$-$C_4$ alkyl-phenyl;
$X_2$ is —Z—$X_1$—
wherein Z is selected from —$(CH_2)_a$—$R_x$—$(CH_2)_a$—NH—C(=O)—; —$(CH_2)_a$—CH(($CH_2)_a$—$R_{x1}$)NH—C(=O)—; —$(CH_2)_a$—$(O)_{0-1}$—$R_{x2}$—CH($R_{x3}$)NH—C(=O)—; and —$(CH_2)_b$—$(O)_{0-1}$—$(CH_2)_b$—NH—C(=O)—;
a is an integer from 0 to 6;
b is an integer from 1 to 6;
$R_x$ is selected from phenyl; $C_3$-$C_8$ cycloalkylene; and —C(H)$_{2-x}$(($C_1$-$C_6$alkyl)$_x$)-;
which phenyl, $C_3$-$C_8$ cycloalkylene, or $C_1$-$C_6$alkyl, are optionally substituted 1, 2, 3 or 4 times independently with $C_1$-$C_6$alkyl, $C_1$-$C_6$alkoxy, $C_1$-$C_6$ haloalkyl or halo;
$R_{x1}$ is selected from phenyl; $C_3$-$C_8$ cycloalkyl; and naphthyl;
which phenyl, $C_3$-$C_8$ cycloalkyl, or naphthyl are optionally substituted 1, 2, 3 or 4 times independently with $C_1$-$C_6$alkyl, $C_1$-$C_6$alkoxy, $C_1$-$C_6$ haloalkyl or halo;
$R_{x2}$ is selected from phenyl; and $C_3$-$C_8$ cycloalkylene;
which phenyl, or $C_3$—C cycloalkylene, are optionally substituted 1, 2, 3 or 4 times independently with $C_1$-$C_6$alkyl, $C_1$-$C_6$alkoxy, $C_1$-$C_6$ haloalkyl or halo;
$R_{x3}$ is selected from hydrogen; phenyl; and $C_3$-$C_6$cycloalkyl,
which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;
x is an integer from 0 to 2;

$R^1$, $R^2$ and $R^3$ are each independently a $C_1$-$C_6$ alkyl, preferably $R^1$, $R^2$ and $R^3$ are each methyl.

In a further embodiment, the cationic moiety is a compound of formula (I), wherein R is hydrogen;

Y is C(O);

X is $X_1$ or $X_2$, wherein $X_1$ is a $C_1$-$C_{20}$ alkylene chain, wherein the chain is straight or branched and is optionally substituted by one or more substituents selected from halogen, —OH, $C_1$-$C_8$ alkoxy, nitro, cyano, —COOH, carbamoyl, —N($R^4$)$R^5$, $C_3$-$C_6$ cycloalkyl, 3 to 7 membered heterocyclic ring, phenyl, 5 or 6 membered heteroaryl, or $C_1$-$C_4$ alkyl-phenyl;

$X_2$ is —Z—$X_1$— wherein Z is selected from —(CH$_2$)$_a$—$R_x$—(CH$_2$)$_a$—NH—C(=O)—; —(CH$_2$)$_a$—CH((CH$_2$)$_a$—$R_{x1}$)NH—C(=O)—; —(CH$_2$)$_a$—(O)$_{0-1}$—$R_{x2}$—CH($R_{x3}$)NH—C(=O)—; and —(CH$_2$)$_b$—(O)$_{0-1}$—(CH$_2$)$_b$—NH—C(=O)—;

a is an integer from 0 to 6;

b is an integer from 1 to 6;

$R_x$ is selected from phenyl; $C_3$-$C_8$ cycloalkylene; and —C(H)$_{2-x}$(($C_1$-$C_6$alkyl)$_x$)-;

which phenyl, $C_3$-$C_8$ cycloalkylene, or $C_1$-$C_6$alkyl, are optionally substituted 1, 2, 3 or 4 times independently with $C_1$-$C_6$alkyl or $C_1$-$C_6$alkoxy;

$R_{x1}$ is selected from phenyl; $C_3$-$C_8$ cycloalkyl; and naphthyl;

which phenyl, $C_3$-$C_8$ cycloalkyl, or naphthyl are optionally substituted 1, 2, 3 or 4 times independently with $C_1$-$C_6$alkyl or $C_1$-$C_6$alkoxy;

$R_{x2}$ is selected from phenyl; and $C_3$-$C_8$ cycloalkylene;

which phenyl, or $C_3$—C cycloalkylene, are optionally substituted 1, 2, 3 or 4 times independently with $C_1$-$C_6$alkyl or $C_1$-$C_6$alkoxy;

$R_{x3}$ is selected from hydrogen; phenyl; and $C_3$-$C_6$cycloalkyl, which phenyl or $C_3$-$C_6$cycloalkyl are optionally substituted 1, 2, 3 or 4 times independently with $C_1$-$C_6$alkyl or $C_1$-$C_6$alkoxy;

x is an integer from 0 to 2;

$R^1$, $R^2$ and $R^3$ are each independently a $C_1$-$C_6$ alkyl, preferably $R^1$, $R^2$ and $R^3$ are each methyl.

In a further embodiment, the cationic moiety is a compound of formula (I), wherein R is hydrogen;

Y is C(O);

X is $X_1$ or $X_2$, wherein $X_1$ is a $C_1$-$C_{20}$ alkylene chain, wherein the chain is straight or branched and is optionally substituted by one or more substituents selected from halogen, —OH, $C_1$-$C_8$ alkoxy, nitro, cyano, —COOH, carbamoyl, —N($R^4$)$R^5$, $C_3$-$C_6$ cycloalkyl, 3 to 7 membered heterocyclic ring, phenyl, 5 or 6 membered heteroaryl, or $C_1$-$C_4$ alkyl-phenyl;

$X_2$ is —Z—$X_1$— wherein Z is selected from -phenyl-CH$_2$—NH—C(O)—; —CH$_2$—C(CH$_2$)$_{2-5}$—CH$_2$—NH—C(O)—; —CH(CH$_2$-naphthyl)-NH—C(O)—; —CH$_2$—O-phenyl-CH($R_z$)—NH—C(O)—;

wherein $R_z$ is phenyl optionally substituted by 1 or 2 substituents independently selected from $C_1$-$C_6$alkyl, and $C_1$-$C_6$alkoxy;

$R^1$, $R^2$ and $R^3$ are each independently a $C_1$-$C_6$ alkyl, preferably $R^1$, $R^2$ and $R^3$ are each methyl.

In a further embodiment, the cationic moiety is a compound of formula (I), wherein R is hydrogen;

Y is C(O);

X is $X_1$ or $X_2$, wherein $X_1$ is an unsubstituted $C_1$-$C_{20}$ alkylene chain, wherein the chain is straight or branched;

$X_2$ is —Z—$X_1$— wherein Z is selected from -phenyl-CH$_2$—NH—C(O)—; —CH$_2$—C(CH$_2$)$_{2-5}$—CH$_2$—NH—C(O)—; —CH(CH$_2$-naphthyl)-NH—C(O)—; —CH$_2$—O-phenyl-CH($R_z$)—NH—C(O)—;

wherein $R_z$ is phenyl optionally substituted by 1 or 2 substituents independently selected from $C_1$-$C_6$alkyl, and $C_1$-$C_6$alkoxy;

$R^1$, $R^2$ and $R^3$ are each independently a $C_1$-$C_6$ alkyl, preferably $R^1$, $R^2$ and $R^3$ are each methyl.

In a further embodiment of the invention, there is provided a method of reacting a DNA-conjugated compound using one or more non-aqueous solvents, wherein the method includes the steps of adsorbing the DNA-labelled compound onto a solid support as defined in any of the previous embodiments and reacting the supported DNA-labelled compound with a reagent in a non-aqueous solvent system. In a further embodiment of the method, the method further includes the step of releasing the product from the solid support.

In a further embodiment of the invention, there is provided the use of a solid support as defined in any of the previous embodiments to support a DNA-conjugated compound. In a further embodiment, there is provided the use of a solid support as defined in any of the previous embodiments to adsorb a DNA-conjugated compound.

Definitions

As used herein, the term "$C_1$-$C_{20}$alkylene" refers to a straight or branched hydrocarbon chain bivalent radical consisting solely of carbon and hydrogen atoms, containing no unsaturation, having from one to twenty carbon atoms.

As used herein, the term "$C_1$-$C_8$alkyl" refers to a straight or branched hydrocarbon chain radical consisting solely of carbon and hydrogen atoms, containing no unsaturation, having from one to eight carbon atoms, and which is attached to the rest of the molecule by a single bond. The term "$C_1$-$C_6$alkyl" is to be construed accordingly.

As used herein, the term "$C_2$-$C_{20}$alkenylene" refers to a straight or branched hydrocarbon chain bivalent radical group consisting solely of carbon and hydrogen atoms, containing at least one double bond, having from two to twenty carbon atoms.

As used herein, the term "$C_2$-$C_{20}$alkynylene" refers to a straight or branched hydrocarbon chain bivalent radical group consisting solely of carbon and hydrogen atoms, containing at least one triple bond, having from two to twenty carbon atoms.

As used herein, the term "$C_3$-$C_8$cycloalkylene" refers to a saturated, monocyclic, bivalent radical hydrocarbon group of 3-8 carbon atoms. In certain embodiments, the $C_3$-$C_8$cycloalkylene group may be bonded via the same carbon atom or via different carbon atoms of the $C_3$-$C_8$cycloalkylene group. Examples of $C_3$-$C_8$cycloalkylene include cyclopropylene, cyclobutylene, cyclopentylene, cyclohexylene, cycloheptylene and cyclooctylene.

As used herein, the term "$C_1$-$C_8$ alkoxy" refers to a radical of the formula —ORa where Ra is a $C_1$-$C_8$alkyl radical as generally defined above. The term $C_1$-$C_6$alkoxy is to be construed accordingly.

As used herein, the term "halo" refers to fluoro, chloro, bromo or iodo. Preferably, halo is fluoro or chloro. More preferably, halo is fluoro.

As used herein, the term "$C_1$-$C_6$ haloalkyl" refers to a $C_1$-$C_6$alkyl radical, as defined above, substituted by one or more halo radicals, as defined above. Examples of $C_1$-$C_6$ haloalkyl include, but are not limited to, trifluoromethyl, difluoromethyl, fluoromethyl, trichloromethyl, 1,1-difluoroethyl, 2,2-difluoroethyl, 2,2,2-trifluoroethyl, 2-fluoropropyl, 3,3-difluoropropyl and 1-fluoromethyl-2-fluoroethyl. Preferably, the halo radical is fluoro.

As used herein, the term "$C_3$-$C_8$cycloalkyl" refers to a saturated monocyclic hydrocarbon group of 3-8 carbon atoms. In an embodiment, $C_3$-$C_8$cycloalkyl is selected from cyclopropyl, cyclobutyl, cyclopentyl, cyclohexyl, cycloheptyl and cyclooctyl. The term "$C_3$-$C_6$cycloalkyl" is to be construed accordingly.

As used herein, the term "—C(O)$C_1$-$C_8$alkyl" refers to a radical of the formula —Ra1-$C_1$-$C_8$alkyl where Ra1 is a carbonyl radical and $C_1$-$C_8$alkyl is as defined above.

As used herein, the term "5 to 10 membered heterocyclic ring" refers to a stable non-aromatic monocyclic or bicyclic ring radical. In an embodiment the 5 to 10 membered heterocyclic ring comprises 1, 2, or 3, heteroatoms individually selected from nitrogen, oxygen and sulfur. The heterocyclyl radical may be bonded via a carbon atom or heteroatom. Examples of heterocyclyl include, but are not limited to, pyrrolinyl, pyrrolidyl, tetrahydrofuryl, tetrahydrothienyl, piperidyl, piperazinyl, tetrahydropyranyl, morpholinyl or perhydroazepinyl. The term "3 to 7 membered heterocyclic ring" is to be construed accordingly.

As used herein, the term "5 or 6 membered heteroaryl" refers to a 5- or 6-membered aromatic monocyclic ring radical. In an embodiment the 5 or 6 membered heteroaryl comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

In an embodiment, "carbamoyl" is a group of formula —C(=O)—NH$_2$.

As used herein, the term "optionally substituted" includes unsubstituted or substituted.

In embodiments whereby $R_x$ or $R_{x2}$ is phenyl, naphthyl or anthracyl, it will be understood that such phenyl, naphthyl or anthracyl groups are bivalent radical groups. The polyethylene glycol-based solid resins may be a cross-linked polyethylene glycol polymer or a pegylated polymer matrix.

Examples of cross-linked PEG-based solid resins include the commercially available NovaPEG/Chemmatrix resins having the formula (IV):

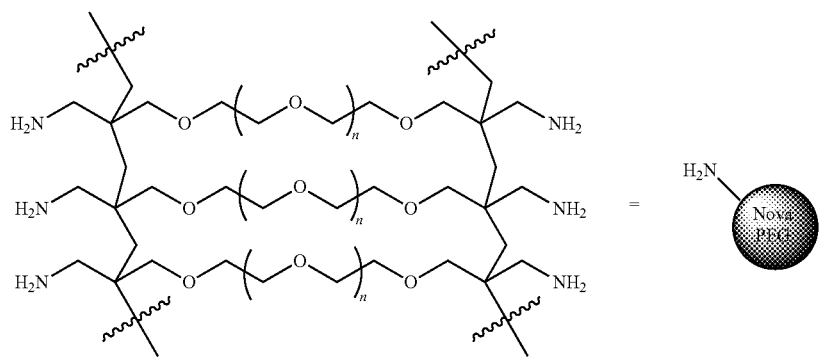

"Halogen" or "halo" refers to fluoro, chloro, bromo or iodo. Preferably, halo is fluoro, chloro or bromo. More preferably, halo is fluoro or chloro.

wherein the solid resin is available with the free amine groups or with functionalized amines which can be reacted to incorporate the cationic moiety discussed above;

and the commercially available PEGA resin (CAS 372109-59-6) having the formula (V):

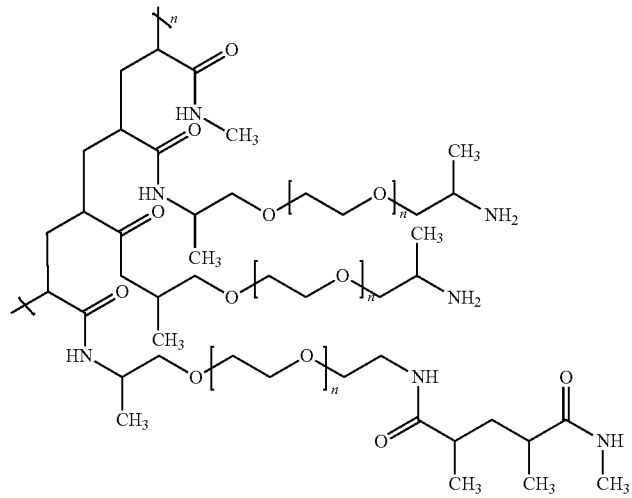

An example of a pegylated solid polymeric resin is the TentaGel® XV—NH$_2$ resin having the formula (VI) (FIG. 1).

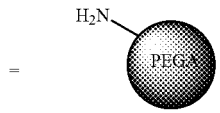

The solid resin bodies are amphiphilic and therefore are well-solvated and compatible with the use of polar solvents (such as water, DMSO, alcohols, etc.) and non-polar organic solvents (such as DCM, THF, acetonitrile, etc.).

Thus, a solid support as defined herein is a solid material comprising a body formed from a plurality of polyethylene glycol (PEG) units and which body further comprises at least one cationic moiety. The solid supports of the invention are insoluble in both aqueous and organic media and are inert to reaction chemistry in which the supports are utilized.

The cationic moiety is any group which bears a positively charged ion capable of adsorbing DNA. Typical examples of cations include, onium cations, such as quaternary ammonium, superbase-conjugate cations, such as guanidinium, amidinium. It will be appreciated by the skilled person that the cationic moiety also encompasses latent cations such as certain superbase-conjugate cations, for example, guanidinium (from a guanidine moiety). The guanidium cation may be formed during the initial step of DNA adsorption complex formation in the presence of water, thereby providing at least one cationic moiety capable of adsorbing DNA.

Adsorption and Release of the DNA-Conjugated Molecules

As noted above, the PEG-based solid resins of the invention are efficiently solvated in water. This permits the DNA-conjugated molecules to be incubated with the solid support suspended in water. The mixture of the DNA-conjugated molecules and the PEG-based solid resin support are agitated together in water for about 15 minutes and the adsorption of the DNA-conjugated molecules onto the PEG-based solid resin support is confirmed by UPLC-TOF analysis of the supernatant or measuring the absorbance of the supernatant after decanting the suspension.

After the DNA-conjugated molecules have been immobilized on the PEG-based solid resin support, they can be dried and suspended in a non-aqueous organic solvent by first washing the resin with a water-miscible solvent (e.g. THF, DMSO, acetonitrile, DMF, an alcohol, etc.), followed by washing the resin with the organic solvent that is to be used in the subsequent reaction (e.g. DCM, dichloroethane, toluene, etc.). Typically, at least three separate washing steps are carried out with the water-miscible solvent, followed by at least three separate washing steps with the organic solvent.

The desired chemical reaction can then be carried out using the immobilised DNA-conjugated molecules in the desired organic solvent in order to transform the DNA-conjugated molecule.

Finally, the DNA-conjugated molecule is released from the resin by known methods, such as two or more treatments of the resin with a concentrated solution of salt (1.5-3M NaCl/0.005% Triton-X100 in water), whereby the solid support may be separated from the newly transformed DNA-conjugate, for example, by filtration.

Therefore, the skilled person would understand that in order for the solid support of the present invention to be suitable for use in non-aqueous DNA-conjugated molecule reactions, the solid support should be insoluble in both aqueous and organic media.

Preparation of Examples

The following Examples have been prepared, isolated and characterized using the methods disclosed herein.

Abbreviations

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "nm" for nanometer or nanometers, "L" for liter or liters, "mL" or "ml" for milliliter or milliliters, "ul", "uL", "µl", or "µL" for microliter or microliters, "nL" or "nl" for nanoliter or nanoliters, ""N" for normal, "uM" or "µM" micromolar, "nM" for nanomolar, "mol" for mole or moles, "mmol" for millimole or millimoles, "min" for minute or minutes, "h" or "hrs" for hour or hours, "RT" for room temperature, "ON" for overnight, "atm" for atmosphere, "psi" for pounds per square inch, "conc." for concentrate, "aq" for aqueous, "sat" or "sat'd" for saturated, "MW" for molecular weight, "mw" or "µwave" for microwave, "mp" for melting point, "Wt" for weight, MS" or "Mass Spec" for mass spectrometry, "ESI" for electrospray ionization mass spectroscopy, "HR" for high resolution, "HRMS" for high resolution mass spectrometry, "LCMS"

for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "1H" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "r", "S", "s", "E", and "Z" are stereochemical designations familiar to one skilled in the art.

The following abbreviations used herein below have the corresponding meanings:

ACN acetonitrile
AcOH acetic acid
$Ac_2O$ acetic anhydride
Bn benzyl
Boc tert-butoxy carbonyl
$Boc_2O$ di-tert-butyl dicarbonate
Bu butyl
$Cs_2CO_3$ cesium carbonate anhydrous
DCE 1,2-dicloroethane
DCM dichloromethane
DIC N,N'-Diisopropylcarbodiimide
DIPEA diisopropylethylamine
DMF dimethylformamide
DMSO dimethylsulfoxide
EDTA ethylenediaminetetraacetic acid
Equiv. equivalence
Et ethyl
EtOH ethanol
HATU 2-(7-Aza-1H-benzotriazole-1-yl)-1,1,3,3-tetramethyluronium hexafluorophosphate
HCl hydrochloric acid
HCOOH formic acid
HFIP 1,1,1,3,3,3-Hexafluoro-2-propanol
HOAt 1-Hydroxy-7-azabenzotriazole
i-Pr isopropyl
iPrOH isopropyl alcohol
$Ir[dF(CF_3)ppy]_2(dtbbpy)PF_6$ [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate
KCN potassium cyanide
$K_2CO_3$ potassium carbonate
Me methyl
MeCN acetonitrile
MeOH methanol
MS molecular sieves or mass spectrometry
$NEt_3$ triethylamine
$NH_3$ Ammonia
$NiCl_2$(dme) nickel(II) chloride ethylene glycol dimethyl ether complex
NMP N-methyl-2-pyrrolidone
Ph phenyl
RT room temperature (° C.)
Rt retention time
t-Bu or $Bu^t$ tert-butyl
TEA triethylamine
TIS triisopropylsilane
TFA trifluoroacetic acid
THF tetrahydrofuran Synthesis of the PEG-Based Solid Supports According to the Invention The base resin is typically a commercially available PEG-based solid resin which includes functionalizable amine groups. The functionalizable amine groups are then derivatized by standard amide coupling procedures (e.g. HATU/DIPEA) to introduce one or more cationic groups as defined hereinabove.

General Protocol for the Kaiser Test for the Detection of Unreacted Amines Remaining after Amide Coupling:

Solution 1: 5 g ninhydrin in 100 mL ethanol
Solution 2: 80 g phenol in 20 mL ethanol
Solution 3: 2 mL 0.001 M aqueous KCN in 98 mL pyridine A few beads are placed in an eppendorf tube and 25(50) μL of each solution are added. The tube was placed in a thermomixer and the reaction left to develop for 5 min at 100° C. Resin and solution blue in colour (variable intensity—from light to dark blue) signifies the reaction isn't complete (positive). Resin and solution colourless to light yellow signifies the reaction is complete (negative).

Example 1

Synthesis of the Cationic Acid 10-Carboxy-N,N,N-Trimethyldecan-1-Aminium Bromide

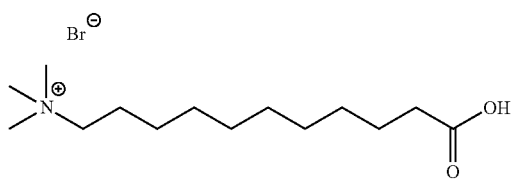 [SMILES: [Br-] ; C[N+](C)(C)CCCCCCCCCCC(=O)O]

11-Bromoundecanoic acid (Fluka CAS 2834-05-1) (8 g, 30.2 mmol) was dissolved in trimethylamine (35% in EtOH) (60 ml, 224 mmol) and the reaction vessel sealed with a septum and the solution stirred at room temperature for 48 hours. A white precipitate formed at this stage. The white precipitate was filtered and washed with cold EtOH. The collected white solid was recrystalized from EtOH, filtered and dried under reduced pressure to afford pure 10-carboxy-N,N,N-trimethyldecan-1-aminium bromide as a white powder.

$^1$H NMR (400 MHz, DMSO-d6) δ 3.30-3.24 (m, 2H), 3.04 (s, 9H), 2.19 (t, J=7.3 Hz, 2H), 1.71-1.60 (m, 2H), 1.48 (t, J=7.1 Hz, 2H), 1.27 (d, J=11.5 Hz, 12H).

UPLC-MS: 0.51 min; 244.3 (M)+. (2_MIN_REACTION_MONITORING_IPA):Waters UPLC Acquity; column: Acquity UPLC BEH C18, 1.7 μm, 2.1×50 mm at 80° C., Eluent A: $H_2O$+0.05% HCOOH+3.75 mM ammonium acetate, B: iPrOH+0.05% HCOOH, Gradient: 5-98% B in 1.7 min, flow: 0.6 mL/min. Rt 0.51 min observed Mw 244.3 (M)+.

Example 2

A commercially available NovaPEG resin Rink amide was obtained. The resin NovaPEG resin Rink amide (250 mg) (0.250 g, 0.115 mmol) was swelled in DMF for 3 hours.

The resin was transformed by mixing the cationic acid:

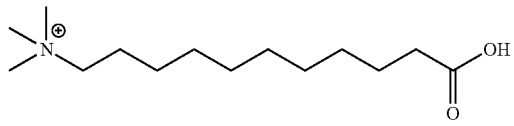 [SMILES: C[N+](C)(C)CCCCCCCCCCC(=O)O]

(0.460 mmol), HOAt (0.063 g, 0.460 mmol), and DIC (0.072 mL, 0.460 mmol) in DMF (Volume: 5 mL)/DMSO (Volume: 3 mL). The resulting solution was added to the resin and allowed to react for 2 hours. The process was repeated once using only DMSO as solvent. A Kaiser test for the detection of free amines was negative.

The resulting derivatized resin:

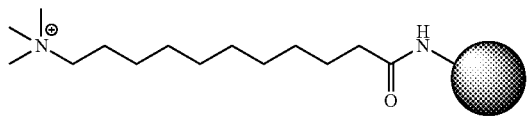

was washed with DMSO four times and water four times.

Example 3

In embodiments in which the derivatization of the amine with the desired cationic acid is more difficult, the following procedure may be used:

In a 50 mL cartridge, the commercially available resin was rinsed with DMSO (Volume: 6 ml).

To a solution of the cationic acid (0.800 mmol) in DMSO (Volume: 6 ml) was added HATU (0.304 g, 0.800 mmol) and DIPEA (0.140 ml, 0.800 mmol). The resulting solution was added to the resin and shaken at 40° C. overnight.

The resin was then filtered and rinsed with DMSO and it was treated again with a fresh solution of reagents at 40° C. for 20 h. The resin was then filtered and rinsed with DMSO. It was then treated with a further solution of the cationic acid (0.800 mmol), Oxyma (0.114 g, 0.800 mmol), DIC (0.125 ml, 0.800 mmol) and DIPEA (0.140 ml, 0.800 mmol) in DMF (Volume: 8 ml) at 60° C. for 2.5 h.

The resulting derivatized resin was then washed with DMF four times, followed by water four times.

Again, a Kaiser test was carried out to determine the coupling on the resin.

Example 4

The skilled person will appreciate that some of the cationic moieties defined above may be formed from oligopeptides, such as oligo-lysines or oligo-arginines. In such instances, the oligopeptides may be grafted onto the solid polymer matrix using an automated peptide synthesizer.
Derivatized Resins Having the Formula:

Resin-NH-Arg-Arg-Arg-Arg-NHAc were prepared for each of the NovaPEG Amino resin, the Amino PEGA resin and the Tentagel XV $NH_2$ resin using the following procedure:

DMF was used as the main solvent for the amino acids (AA), the Activator (Act) and Base.
Coupling:

A LibertyBlue Synthesizer was loaded with amino acid (0.2M), Activator (DIC—0.5M), Base (Oxym (1M)+DIPEA (0.1M)) in the ratio resin/AA/Act/Base: 1/5/5/5 (total volume 4 ml). The synthesizer was operated in accordance with the manufacturer's instructions at a temperature of 90° C.
Deprotection:

The compounds were deprotected using 10% piperidine in NMP/EtOH (9/1).
Capping:

A capping solution of $Ac_2O$ (5 mmol) and DIPEA (5 mmol) in DMF (5 ml) was used. The resin was treated with the capping solution and shaken for 1 h at 25° C. The resin was then filtered and washed with DCM.
Deprotection of the Arg (Pbf):

The resin was treated with a 5 ml solution of TFA/TIS/water (90:5:5) and shaken at 25° C. for 1 h. The resin was then filtered and washed with DCM, THF and water.

Example 5

Synthesis of the Different Cationic Resins with Different Linkers

Synthesis can be carried out from commercially available NovaPEG amino resin (Merck product number 8.55126) Loading 0.57 mmol/g (F. Garcia-Martin, et al. (2006) J. Comb. Chem., 8, 213.).

Example 5.1

Amino-PEG-$N^+(Me)_3$

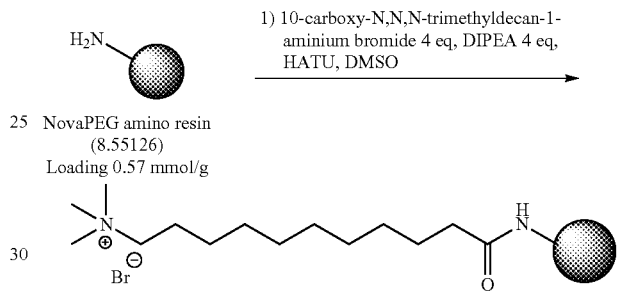

NovaPEG amino resin (250 mg, 0.143 mmol) was suspended in a 25 mL syringe (equipped with a filter) using DCM (Volume: 10.00 mL). The syringe was shaken at room temperature for 3 h, filtered and washed 3 times with DMSO. 10-carboxy-N,N,N-trimethyldecan-1-aminium bromide (185 mg, 0.570 mmol), DIPEA (N,N-diisopropylethylamine) (0.099 mL, 0.570 mmol) and HATU (223 mg, 0.570 mmol) were premixed in DMSO (Volume: 5 mL), shaken for 2 min at rt and added to the resin. The resulting suspension was shaken at room temperature for 16 h. Workup: The resin was washed 4× with DMSO.

The performed Kaiser test was negative. The resin was then washed 2× with $H_2O$/glycerol (1/1) and swelled overnight in 10 mL of this solution. The suspension was then filtered, washed 2 times with the same solution and filtered to dryness. The resin was transferred from the syringe to a 15 mL Falcon tube with 2×2.5 mL $H_2O$/glycerol (1/1).
Synthesis of the Different Cationic Resins with Different Linkers —Z—$X_1$—

Example 5.2

PEG-Bn-$N^+(Me)_3$

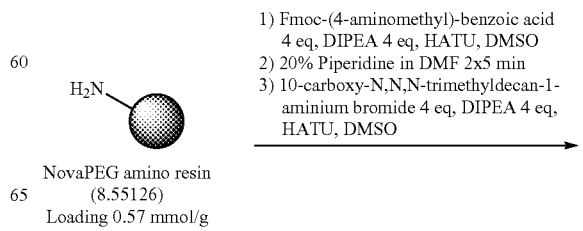

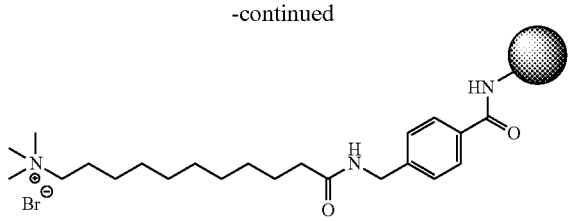

The NovaPEG amino resin (250 mg, 0.115 mmol) was swelled in 10 mL DCM for 1 h, then washed 2 times with 5 mL DMSO. In a separate flask the acid was activated by mixing Fmoc-(4-aminomethyl)-benzoic acid (175 mg, 0.460 mmol), DIPEA (N,N-diisopropylethylamine) (59.5 mg, 0.460 mmol) and HATU (180 mg, 0.460 mmol) in DMSO (Volume: 5 mL). The resulting solution was added to the resin and allowed to react for 12 hours at room temperature with shaking. The coupling reaction was repeated. The Kaiser test for the detection of unreacted amines was negative. To eliminate any remaining primary amine the resin was capped by treatment with a solution of acetic anhydride/N,N-diisopropylethylamine/DMF 1/2/7 vol/vol/vol) for 15 min. The resin was washed 4× with DMSO.

Deprotection of the Fmoc-group: To the resin 10 mL of 20% (v/v) piperidine in DMF was added. The mixture was shaken at room temperature for 5 minutes. The resin was then filtered. A second portion of 20% piperidine in DMF was added and the mixture was shaken at room temperature for 5 minutes. The resin was filtered and washed with several portions of DMSO. The compound 10-carboxy-N,N,N-trimethyldecan-1-aminium bromide (146 mg, 0.450 mmol), DIPEA (N,N-diisopropylethylamine) (0.078 mL, 0.450 mmol) and HATU (176 mg, 0.450 mmol) were premixed in DMSO (Volume: 5 mL), shaked for 2 min at rt and added to deprotected resin. The resulting suspension was shaken at room temperature for 16 h. The resin was washed 4 times with DMSO. The Kaiser test was negative. The resin was then washed 2 times with H$_2$O/glycerol (1/1) and swelled over night in 10 mL of this solution. The suspension was then shaken at 60° C. for 1 h and filtered to dryness. The resin was transferred from the syringe to a 15 mL Falcon tube with 2×2.5 mL H$_2$O/glycerol (1/1).

Example 5.3

PEG-Cyclohexane-N$^+$(Me)$_3$

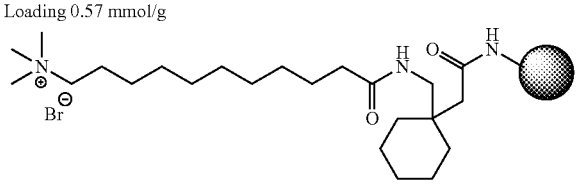

1) Boc-1-aminomethyl-cyclohexane acetic acid 4 eq, DIPEA 4 eq, HATU, DMSO
2) 50% (v/v) TFA/dichloromethane (DCM) 2×5 min
3) 10-carboxy-N,N,N-trimethyldecan-1-aminium bromide 4 eq, DIPEA 4 eq, HATU, DMSO NovaPEG amino resin (8.55126)
Loading 0.57 mmol/g The NovaPEG amino resin (250 mg, 0.115 mmol) was swelled in 10 mL DCM for 1 h, and then washed 2 times with 5 mL DMSO. The acid Boc-1-aminomethyl-cyclohexane acetic acid (125 mg, 0.460 mmol) was activated by treatment with DIPEA (N,N-diisopropylethylamine) (0.082 mL, 0.460 mmol) and HATU (180 mg, 0.460 mmol) in DMSO (Volume: 5 mL). The resulting solution was added to the resin and allowed to react for 12 h at room temperature with shaking. The coupling reaction was repeated. To remove the any remaining primary amine the resin was capped by treatment with a solution of acetic anhydride/N,N-diisopropylethylamine/DMF 1/2/7 vol/vol/vol) for 15 min. The resin was washed 4× with DMSO. The Kaiser test was negative (resin light yellow and solution light yellow).

Deprotection of the Boc-group: The resin was suspended in 10 mL 50% (v/v) TFA/dichloromethane (DCM) and shaked at room temperature for 3 minutes and filtered. A second portion of 50% TFA/DCM was added and shaken at room temperature for 5 minutes. The resin was washed three times with 10 mL DCM (1 mL/gm resin). The resin was washed three times with 10 mL 5% (v/v) diisopropylethylamine (DIPEA N,N-diisopropylethylamine)/DCM) to remove TFA. The resin was washed four times with DMSO. The compound 10-carboxy-N,N,N-trimethyldecan-1-aminium bromide (146 mg, 0.450 mmol), DIPEA (N,N-diisopropylethylamine) (0.078 mL, 0.450 mmol) and HATU (176 mg, 0.450 mmol) were premixed in DMSO (Volume: 5 mL), shaken for 2 min at rt and added to deprotected resin. The resulting suspension was shaken at room temperature for 16 h. The resin was washed 4 times with DMSO. The Kaiser test was negative. The resin was then washed 2 times with H$_2$O/glycerol (1/1) and swelled overnight in 10 mL of this solution. The suspension was then shaken at 60° C. for 1 h and filtered to dryness. The resin was transferred from the syringe to a 15 mL Falcon tube with 2×2.5 mL H$_2$O/glycerol (1/1).

Example 5.4

PEG-Napht-N$^+$(Me)$_3$

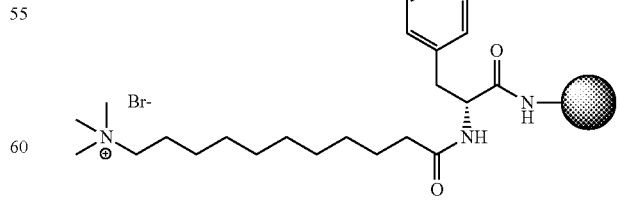

1) N-Fmoc-3-(2-naphthyl)-L-alanine 4 eq, DIPEA 4 eq, HATU, DMSO
2) 20% Piperidine in DMF 2×5 min
3) 10-carboxy-N,N,N-trimethyldecan-1-aminium bromide 4 eq, DIPEA 4 eq, HATU, DMSO NovaPEG amino resin (8.55126)
Loading 0.57 mmol/g The NovaPEG amino resin (250 mg, 0.115 mmol) was swelled in 10 mL DCM for 1 h, then washed 2 times with 5 mL DMSO. The acid was activated by mixing N-Fmoc-3-(2-naphthyl)-L-alanine (212 mg, 0.460 mmol), DIPEA (N,N-diisopropylethylamine) (0.082 mL, 0.460 mmol) and HATU (180 mg, 0.460 mmol) in DMSO (Volume: 5 mL). The resulting solution was added to the resin and allowed to react for 12 hours at room temperature with shaking. The resin was washed 4 times with DMSO. The coupling reaction was repeated. To remove the any remaining primary amine the resin was capped by treatment with a solution of acetic anhydride/N,N-diisopropylethylamine/DMF 1/2/7 vol/vol/vol) for 15 min. The resin was washed 4 times with DMSO. The Kaiser test was negative (resin light yellow and solution light yellow). Deprotection of the Fmoc-group: To the resin 10 mL of 20% (v/v) piperidine in DMF was added. The mixture was shaked at room temperature for 5 minutes. The resin was filtered. A second portion of 20% piperidine in DMF was added and the mixture was shaked at room temperature for 5 minutes. The compound 10-carboxy-N,N,N-trimethyldecan-1-aminium bromide (146 mg, 0.450 mmol), DIPEA (N,N-diisopropylethylamine)(0.078 mL, 0.450 mmol) and HATU (176 mg, 0.450 mmol) were premixed in DMSO (Volume: 5 mL), shaken for 2 min at rt and added to deprotected resin. The resulting suspension was shaken at room temperature for 16 h. The resin was washed 4× with DMSO. The Kaiser test was negative. The resin was then washed 2 times with $H_2O$/glycerol (1/1) and swelled overnight in 10 mL of this solution. The suspension was then shaken at 60° C. for 1 h and filtered to dryness. The resin was then transferred from the syringe to a 15 mL Falcon tube with 2×2.5 mL $H_2O$/glycerol (1/1).

Example 6

Synthesis of different cationic resins with different cationic groups from commercially available NovaPEG resin Rink amide (Merck product number 8.55047) Loading 0.46 mmol/g.

Example 6.1

PEG-$N^+$(Me)$_3$

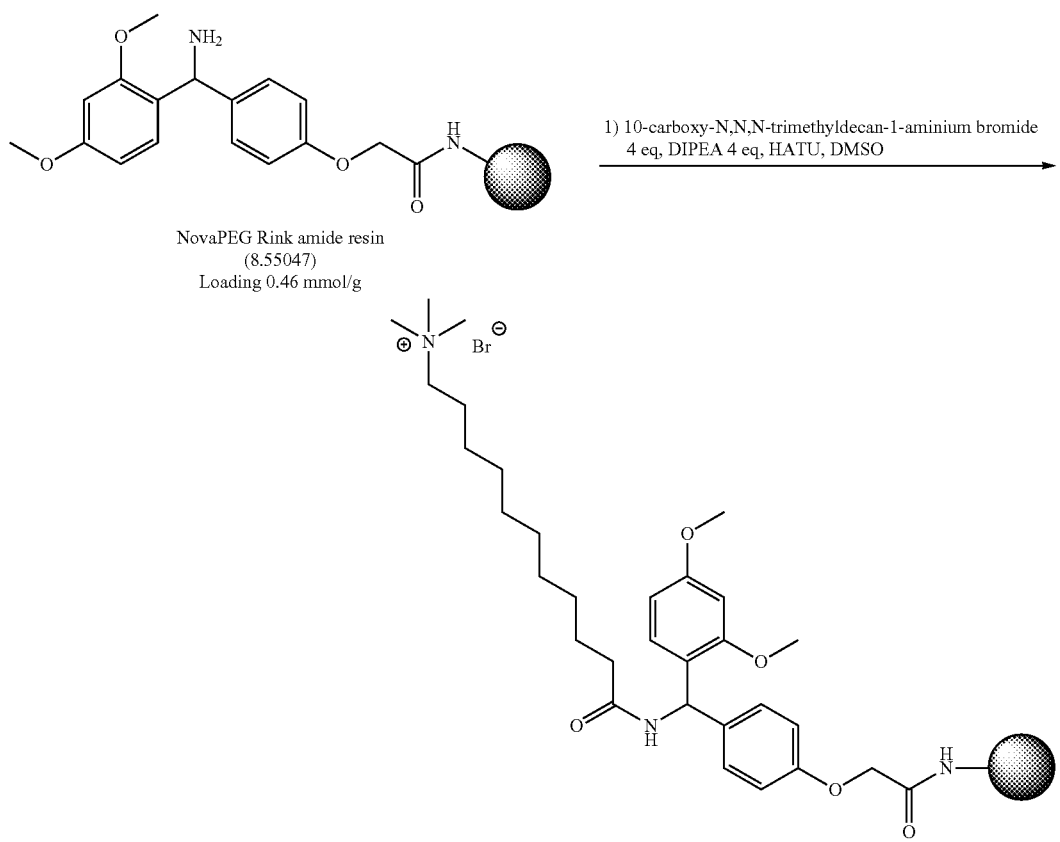

The resin NovaPEG resin Rink amide (250 mg) (4 g, 1.840 mmol) was swelled in DCM for 3 hours. The acid was activated by mixing 10-carboxy-N,N,N-trimethyldecan-1-aminium bromide (2.387 g, 7.36 mmol), HATU (2.80 g, 7.36 mmol) and DIPEA (N,N-diisopropylethylamine) (1.285 mL, 7.36 mmol) in DMSO (Volume: 40 mL). The resulting solution was added to the resin and allowed to react for 12 hours. A Kaiser test for the detection of unreacted amines was negative. The resin was washed 4 times with DMSO and 4 times with water, then suspended in water/glycerol 1/1.

Example 6.2

PEG-N⁺(Et)₃

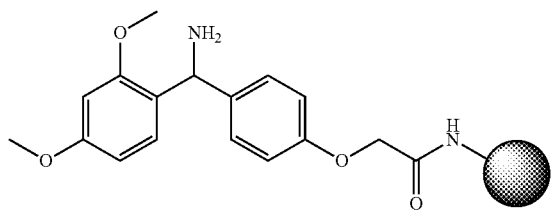

NovaPEG Rink amide resin
(8.55047)
Loading 0.46 mmol/g 1) 11-bromodecanoic acid (Aldrich CAS 2834-05-1)
   4 eq, DIPEA 4 eq, HATU, DMSO
2) triethylamine, Ethanol, reflux

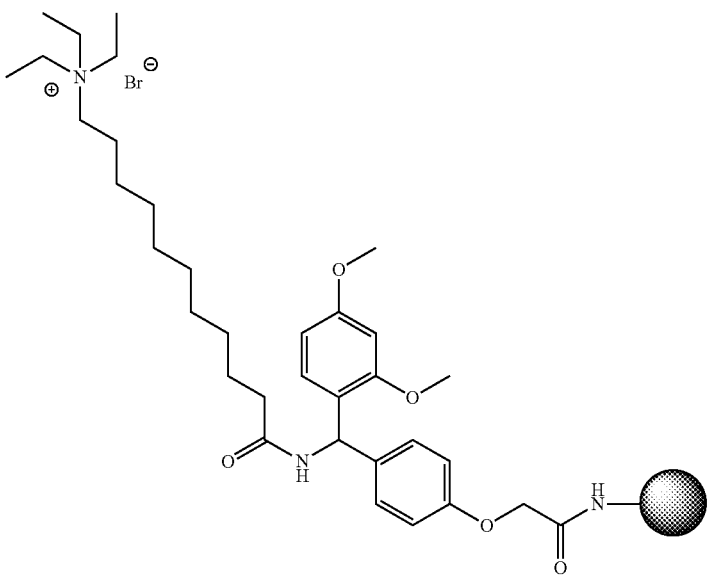

The resin NovaPEG Rink resin (500 mg) (0.5 g, 0.230 mmol) was swelled in DCM for 30 min. The acid 11-bromodecanoic acid (Aldrich CAS 2834-05-1) (0.976 g, 3.68 mmol) was activated by treatment with triethylamine (0.513 mL, 3.68 mmol) and diisopropylcarbodiimide (0.287 mL, 1.840 mmol). The resulting solution was added to the resin and allowed to react for 12 hours at room temperature. A Kaiser test for the detection of unreacted amines was negative. The resin was washed with ethanol 3 times and suspended in 25 ml of 1/1 vol/vol NEt₃/EtOH. This suspension was refluxed for 12 hours. The resin was washed and a capping was performed to remove any residual primary amine (10 min DMF/DIPEA(N,N-diisopropylethylamine)/Ac₂O 7/2/1). Success of the quaternization was determined by a cleavage on a few beads of resin in TFA/Water 95/5 and observation by UPLC-MS of the expected quaternary ammonium carboxamide 11-amino-N,N,N-triethyl-11-oxoundecan-1-aminium bromide and the absence of the corresponding bromo carboxamide 11-bromoundecanamide.

UPLC-MS: 0.61 min (ELSD detection, no chromophore on the molecule); 285.4 (M+). (2_MIN_REACTION_MONITORING_IPA):Waters UPLC Acquity; column: Acquity UPLC BEH C18, 1.7 μm, 2.1×50 mm at 80° C., Eluent A: H₂O+0.05% HCOOH+3.75 mM ammonium acetate, B: iPrOH+0.05% HCOOH, Gradient: 5-98% B in 1.7 min, flow: 0.6 mL/min. Interpreted as compatible with the structure of 11-amino-N,N,N-triethyl-11-oxoundecan-1-aminium bromide. The resin was washed with DMSO 4 times, MeOH, DMF and water 4 times. No further purification was needed and this resin was used as is after adjusting the volume of the suspension in water/glycerol 1/1 to 10 ml.

Example 6.3

PEG-N$^+$(Bu)$_3$

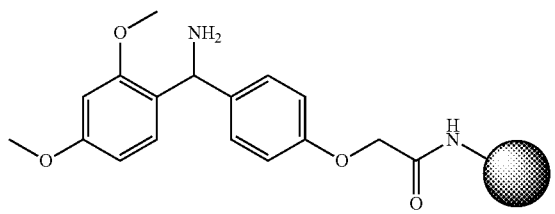

1) 11-bromodecanoic acid (Aldrich CAS 2834-05-1) 4 eq, tributylamine 4 eq, HATU, DMSO
2) Tributylamine NovaPEG Rink amide resin (8.55047)
Loading 0.46 mmol/g

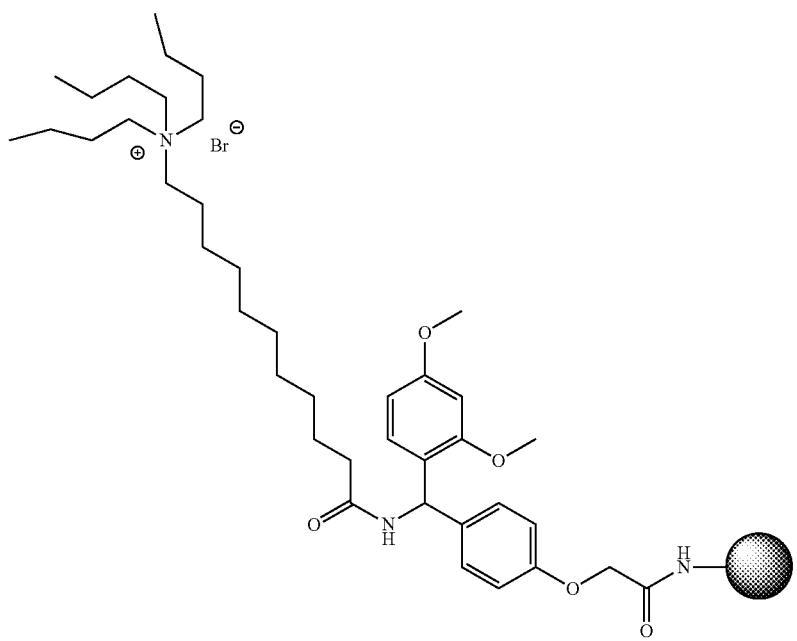

The resin NovaPEG Rink resin (500 mg) (0.5 g, 0.230 mmol) was swelled in DCM for 30 min. The acid 11-bromodecanoic acid (Aldrich CAS 2834-05-1) (0.976 g, 3.68 mmol) was activated by treatment with tributylamine (0.043 g, 0.230 mmol) and DIC (0.287 mL, 1.840 mmol). The resulting solution was added to the resin and allowed to react for 12 h at room temperature. A Kaiser test for the detection of unreacted amines was negative. The resin was washed with ethanol 3 times and suspended in 25 ml of neat tributylamine. This suspension was stirred at 150° C. for 12 h. The resin was washed and a capping was performed (10 min DMF/DIPEA(N,N-diisopropylethylamine)/Ac$_2$O 7/2/1). Success of the quaternization was determined by a cleavage on a few beads of resin and observation by UPLC-MS of the expected quaternary ammonium carboxamide 11-amino-N,N,N-tributyl-11-oxoundecan-1-aminium bromide and the absence of the corresponding bromo carboxamide 11-bromoundecanamide.

UPLC-MS: 0.81 min (ELSD detection, no chromophore on the molecule); 369.4 (M+). (2_MIN_REACTION_MONITORING_IPA):Waters UPLC Acquity; column: Acquity UPLC BEH C18, 1.7 μm, 2.1×50 mm at 80° C., Eluent A: H$_2$O+0.05% HCOOH+3.75 mM ammonium acetate, B: iPrOH+0.05% HCOOH, Gradient: 5-98% B in 1.7 min, flow: 0.6 mL/min. Interpreted as compatible with the structure of 11-amino-N,N,N-tributyl-11-oxoundecan-1-aminium bromide. The resin was washed with DMSO 4 times, MeOH, DMF and water 4 times. No further purification was needed and this resin was then used as is after adjusting the volume of the suspension in water/glycerol 1/1 (vol/vol) to 10 ml.

Example 6.4

PEG-N⁺(Me)₂Bn

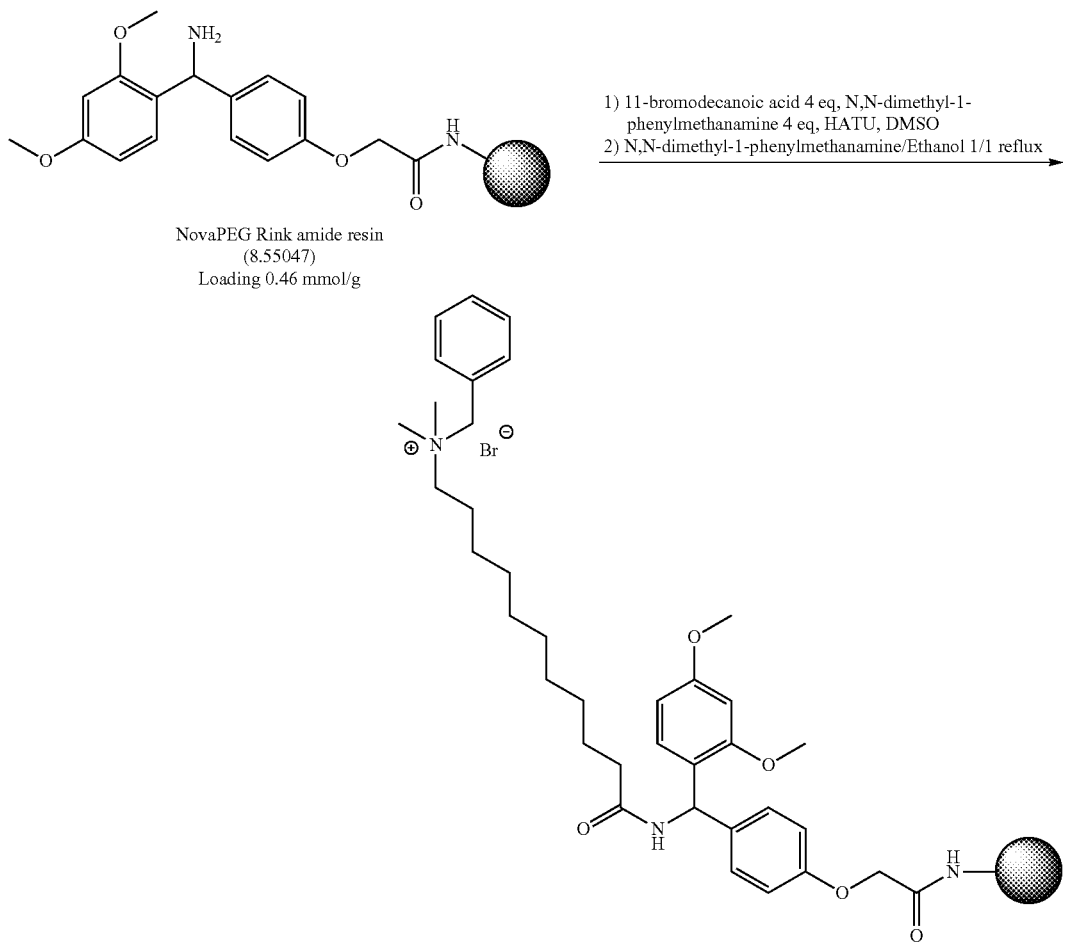

The resin NovaPEG Rink resin (500 mg) (0.5 g, 0.230 mmol) was swelled in DCM for 30 min. The acid was activated by mixing 11-bromodecanoic acid Aldrich CAS 2834-05-1 (0.976 g, 3.68 mmol), N,N-dimethyl-1-phenyl-methanamine (0.554 mL, 3.68 mmol) and DIC (0.287 mL, 1.840 mmol) in DCM (Volume: 8 mL). The resulting solution was added to the resin and allowed to react for 12 hours at room temperature. The process was repeated once. A Kaiser test for the detection of unreacted amines was negative. The resin was washed with ethanol 3 times and suspended in 25 ml of 1/1 Ethanol/N,N-dimethyl-1-phenyl-methanamine (vol/vol). This suspension was refluxed for 12 hours. The resin was washed with Ethanol 3 times and a capping was performed (10 min DMF/DIPEA(N,N-diisopropylethylamine)/Ac₂O 7/2/1). Success of the quaternerization was determined by a cleavage on a few beads of resin and observation by UPLC-MS of the expected quaternary ammonium carboxamide 11-amino-N-benzyl-N,N-dimethyl-11-oxoundecan-1-aminium bromide and the absence of the corresponding bromo carboxamide 11-bromoundecanamide.

UPLC-MS: 0.67 min (ELSD detection); 319.4 (M+) (2_MIN_REACTION_MONITORING_IPA) Waters UPLC Acquity; column: Acquity UPLC BEH C18, 1.7 µm, 2.1×50 mm at 80° C., Eluent A: H₂O+0.05% HCOOH+3.75 mM ammonium acetate, B: iPrOH+0.05% HCOOH, Gradient: 5-98% B in 1.7 min, flow: 0.6 mL/min. Interpreted as compatible with the structure of 11-amino-N-benzyl-N,N-dimethyl-11-oxoundecan-1-aminium bromide. The resin was washed with DMSO 4 times, MeOH, DMF and water 4 times.

These different resins were then used to demonstrate the advantage of using the novel solid supports of the present invention when compared to existing solid supports described in the literature to perform conjugation reactions on oligonucleotides in the absence of water (vide infra).

Reactions Using the Resins of the Invention as a Solid Support

The resins of the subject invention were used to carry out reactions on DNA-conjugated compounds under non-aqueous conditions as follows:

Example 7

SNAP Reaction:

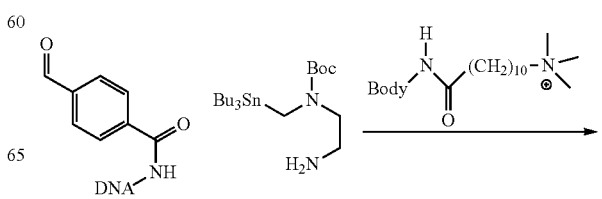

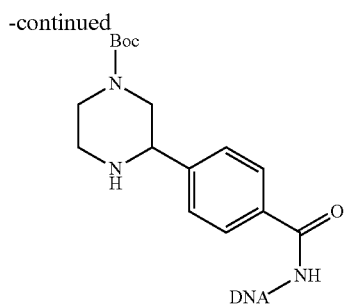

The cationic support resin prepared in Example 1 was initially swollen in water. The resin (250 μL) was then incubated with a solution of the benzaldehyde-DNA conjugate (87 μL) in a 2 ml syringe equipped with a filter for 15 min. The resin was washed with water, THF and DCM (4 times). 0.2 mL of DCM was added to the resin followed by some MS 4A and tert-Butyl (2-aminoethyl)((tributylstannyl)methyl)carbamate (8.42 μL). The suspension was shaken for 30 min at 40° C. then it was rinsed and this treatment was repeated. The resin was rinsed with DCM, DCM (0.16 mL) was added and it was treated with a suspension of copper(II) trifluoromethanesulfonate (0.181 mg) and 2,6-lutidine (0.058 μL) in HFIP (Volume: 0.04 mL) (premixed at RT for 1 h). The suspension was shaken at 40° C. for 2 h.

Workup

The resin was washed 3 times with THF. The DNA was then released from the resin by treatment with 500 μl of DNA elute solution (1.5M NaCl, 50 mM phosphate buffer pH8, 0.005% triton-X). The solution was recovered and diluted with 500 μl of EDTA. 70 ul of this diluted solution was desalted by P6 purification as follows:

1. Invert a prepacked P-6 Column (Micro Bio-Spin™ P-6 Gel Columns, SSC Buffer #732-6205, BioRad) sharply several times to resuspend the settled gel and remove any bubbles
2. Snap off the tip and place the column in a 2.0 ml tube and remove cap.
3. Drain packing buffer by gravity and discard buffer
4. Drain by spinning for 2 min, 1000G≈3.9 rpm
5. Add 500 μL Milli-Q water and drain by spinning for 1 min, 1000G≈3.9 rpm
6. Repeat step 5 (3 times)
7. Apply sample (50-75 μL)
8. Collect purified sample in a fresh eppendorf tube by spinning for 4 min. at 1000G≈3.9 rpm.

The product had a yield of 70%.

Comparative Example 8

The same reaction as described in Example 7 was carried out using a DEAE sepharose support. The reaction conditions were the same as described in Example 7, except that the benzaldehyde-DNA conjugate was supported on a DEAE sepharose support prior to the addition of the tert-Butyl (2-aminoethyl)((tributylstannyl)methyl)carbamate.

The product using the DEAE sepharose support resulted in a product yield of less than 10%.

Example 9

Ruthenium Catalysed Addition of a Carbanion

Owing to its potential scope and building block availability, this reaction was of particular interest and was chosen as a further example to test the concept of using cationic resins under non-aqueous condition. This novel methodology operates under mild conditions in pure organic solvents, but was not even described to be compatible with the presence of air or water. Using a ketone-DNA conjugate immobilized on a PEG-based cationic resin, we were able to test this methodology and quickly obtained almost quantitative conversion after only a few rounds of optimization as follows:

Wherein:
1 is hydrazine hydrate
2 is Dichloro(p-cymene)ruthenium (II) dimer
3 is 1,3-bis(diphenylphosphino)propane (DPPP)
4 is potassium phosphate or calcium carbonate
5 is the resin used in Example 7

Preparation of Solution A:

Benzaldehyde (Aldrich CAS 100-52-7) (488 μL) was dissolved in THF (Volume: 2 mL) followed by the addition of hydrazine (233 μL). This solution was stirred at room temperature for 30 min. A small amount of $Na_2SO_4$ (580 mg) was added to this solution before using it to dissolve Dichloro(p-cymene)ruthenium(II) dimer (Aldrich CAS 52462-29-0) (18 mg) and 1,3-Bis(diphenylphosphino)propane (Aldrich CAS 6737-42-4) (25 mg).

Preparation of Supported Ketone-DNA Conjugate:

In a syringe 200 μl of a suspension of the cationic resin prepared in Example 2 (resin swollen in water) (200 μL) was incubated with 97 μl of a solution of the ketone-DNA conjugate (as a solution in water) (0.064 mg) for 15 min. The resin was washed with water and THF (4 times).

Ruthenium Catalysed Carbanion Addition:

500 µl of Solution A was then added to this supported ketone-DNA conjugate, followed by the addition of solid $K_3PO_4$ (79 mg) and stirred at 45° C. for 1 hour.

The solvent was then drained and the resin was washed three times with THF before releasing the DNA-substrate using the workup procedure described above in Example 7.

The DNA substrate was recovered with a yield of 75%.

Comparative Example 10

The same reaction as described in Example 9 was carried out using a DEAE sepharose support. The reaction conditions were the same as described in Example 9, except that the ketone-DNA conjugate was supported on a DEAE sepharose support prior to the addition of Solution A.

The reaction of comparative Example 10 yielded no carbanion addition product.

Example 11

Reductive Amination

A reductive amination of a ketone was carried out using dichloromethane as a solvent as follows:

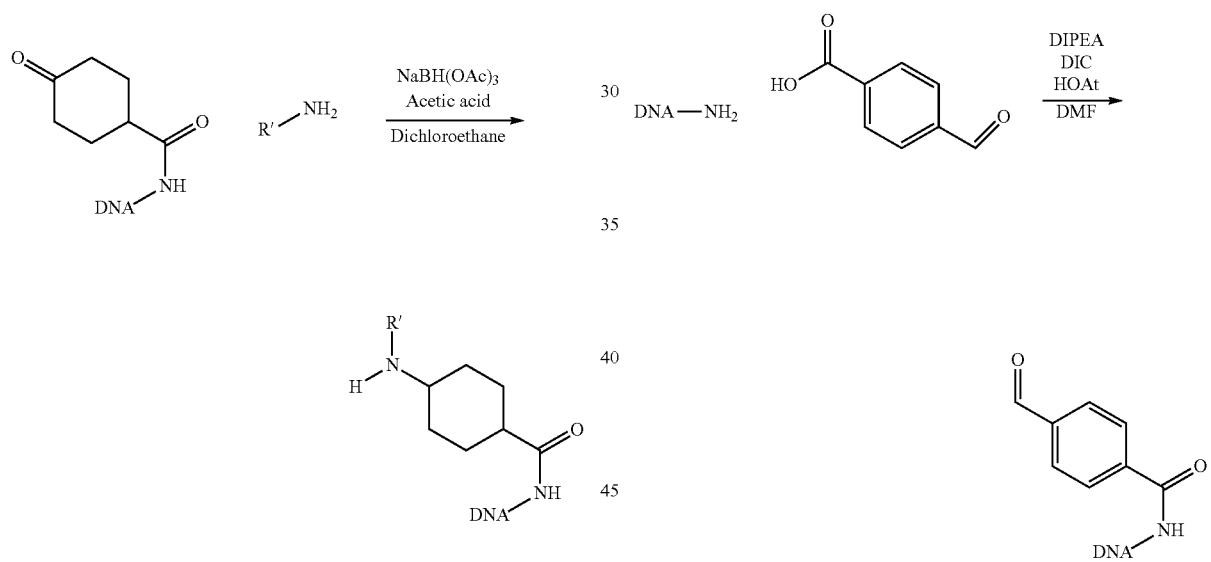

Preparation of Solution A:

Acetic acid was dissolved in dichloroethane (285 mM) and to this was added a solution of the amine in dichloroethane (285 mM).

Preparation of supported ketone-DNA Conjugate:

In a syringe 200 µl of a suspension of the cationic resin prepared in Example 2 (resin swollen in water) (200 µL) was incubated with 97 µl of a solution of the ketone-DNA conjugate (as a solution in water) (0.064 mg) for 15 min. The resin was washed with THF (4 times) and dichloroethane (2 times).

Reductive Amination Reaction:

500 µl of Solution A was then added to the supported ketone-DNA conjugate and the suspension was incubated at room temperature for one hour. After incubation, sodium triacetoxyborohydride (42.4 mg) was added as a solid and the reaction mixture was agitated at room temperature for 2 hours.

The solvent was then drained and the resin was washed three times with DCE and three times with THF. The product was released from the support by treatment with 500 µl of DNA elute solution containing 5% of 4-methylpiperidine and then desalted by the P6 purification method described in Example 7.

In Example 11.1, the amine was aniline (i.e. $R'=C_6H_5—CH_2—$) and the product was recovered in a yield of 87%.

In Example 11.2, the amine was benzylamine (i.e. $R'=C_6H_5—$) and the product was recovered in a yield of 44%.

Example 12

Acylation

A conventional acylation reaction was carried out on a cationic support as follows:

The DNA moiety was supported on the cationic support prepared in Example 2 by placing 250 µl of the resin (swollen in water) in a 1 ml cartridge equipped with a filter and incubating the resin with a solution of the DNA moiety (0.01 µmol) for 15 minutes at room temperature. The resin was washed with water and then with DMF (4 times).

The resin was then treated at room temperature with a solution of 4-formylbenzoic acid (0.450 mg, 3.00 µmol), DIPEA (0.524 µl, 3.00 µmol), DIC (0.467 µl, 3.00 µmol) and HOAt (0.408 mg, 3.00 µmol) in DMF (Volume: 0.2 mL) for 15 min, this treatment was repeated once.

The product was then released from the support and purified using the methods described in Example 7.

Example 13

Synthesis of the Oligonucleotide Conjugate DNA-4-IODO

Molecular Structure of the Oligo-Amine Starting Material

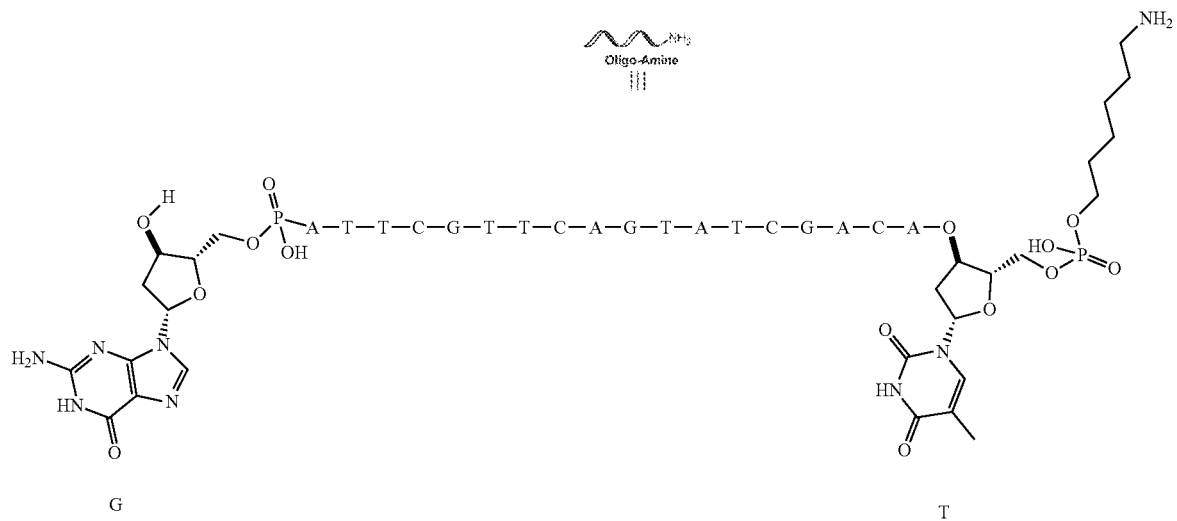

Chemical Formula: $C_{202}H_{262}N_{72}O_{123}P_{20}$
Exact Mass: 6283.12
Molecular Weight: 6286.17

The sequence of this model oligonucleotide (5'-TACAGCTATGACTTGCTTAG-3' (SEQ ID NO: 1)) was randomized.

The acylation protocol on immobilized DNA was adapted from Harbury et al. (Halpin, D. R.; Lee, J. A.; Wrenn, S. J.; Harbury, P. B., DNA Display III. Solid-Phase Organic Synthesis on Unprotected DNA. *PLoS Biology* 2004, 2 (7), e175.).

Acylation Protocol for the Synthesis of DNA-4-IODO

5000 µl of a suspension of DEAE sepharose (DEAE Sephadex™ A-25, GE Healthcare 17-0170-02) was washed with 10 ml of DNA bind solution (10 mM Acetic acid in water+0.005% triton-X100).

5000 ul of a solution of Oligo-Amine as a solution (0.5 nmole/µl) (3.14 mg, 0.5 µmol) was then added to the resin together with 5 ml of DNA bind solution. This suspension was agitated for 2 min, followed by filtration and washing with water (10 ml) and MeOH (10 ml). The resin was then washed for 2 min with 10 ml of a 5% 4-methylpiperidine in MeOH to neutralize and remove any remaining acetic acid.

A solution of activated acid was prepared by mixing HOAt (CAS 39968-33-7)(100 mM in MeOH) (3000 µl, 300 µmol), 4-iodobenzoic acid (100 mM in DMSO) (3000 µl, 300 µmol) and DIC (46.7 µl, 300 µmol). This solution was agitated 30 seconds before addition to the DEAE sepharose resin. The resin was agitated 15 min with the activated acid and this process repeated once. A few beads were then incubated in 65 µl of DNA elute solution (1.5M NaCl, 50 mM pH 8 phosphate buffer in water+0.005% triton-X100) and the released DNA purified by P6 chromatography (Micro Bio-Spin™ P-6 Gel Columns) before HPLC-TOF analy-

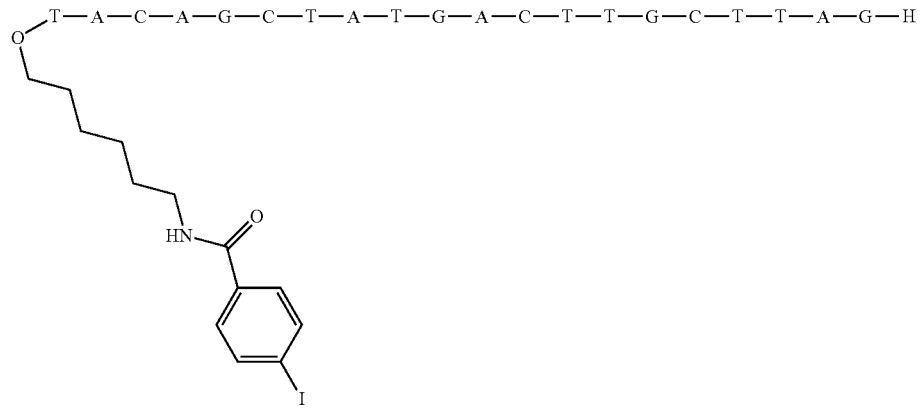

Chemical Formula: $C_{209}H_{265}IN_{72}O_{124}P_{20}$
Exact Mass: 6513.04
Molecular Weight: 6516.18

Molecular Structure of the Starting Material DNA-4-IODO sis. Workup and Purification: At this stage the reaction was complete, and the DNA was released by treatment with 2 ml of DNA elute solution (1.5 M NaCl, 50 mM phosphate buffer pH 8, 0.005% triton-X) for 30 min, followed by 3 treatments with 2000 µl of the same solution for 15 min. The mixture was concentrated using a 3K MWCO Ultrafiltration device (PALL, Nanosep 3K-30K Omega Centrifugal Device, 5 mL, 5000G, 40° C., 30 min). The concentrated sample was diluted to 4 ml with water and concentrated again (5000G, 40° C., 30 min) (twice). The final solution was purified by reverse phase HPLC (Column Xbridge® Prep C18 5 µm OBD™ 19×50 mm, Solvent A: 100 mM HFIP 86 mM TEA, Solvent B: MeOH/ACN 1/1). The fractions were combined and concentrated using a 3K MWCO centrifugal device (5000G, 40 C, 30 min) and adjusted to 4 ml to give a solution containing 445 nmoles of pure product DNA-4-IODO (89%) as determined by the UV absorbance at 260 nm. UPLC/MS: Agilent 6200 series TOF/6500 series Q-TOF, Column ACQUITY BEH OST C18 2.1×50 mm 1.7 um at 60° C., Flow 0.6 mL/min, Gradient: 15-30% B in 2.7 min; 30-85% B in 0.95 min; 85-100% B in 0.05 min; 100% for 0.8 min with A=water+10 mM TEA+200 mM HFIP and B=MeOH, Rt=1.90 min, m/z=6515.97 amu (M after deconvolution with Agilent MassHunter Qualitative Analysis 6.00)(Calc. 6516.05), interpreted as compatible with the structure of the final compound DNA-4-IODO.

The predicted isotope distribution (ChemBioDraw Ultra 14.00) of the product (red) was overlapped with the experimental isotope distribution (blue) using the Isotope Distribution Calculator add-on from the Agilent MassHunter 6.00 software suite.

Example 14

Effect of Added Water and Replacement of PEG-N⁺(Me)₃ by DEAE Sepharose

This experiment aimed to compare PEG-N+(Me)₃ with commercially available ion exchange resin DEAE sepharose (CAS Number 57407-08-6), and to demonstrate that added water is detrimental to organic transformations that are sensitive to the presence of water.

Standard Conditions for Photochemical Decarboxylative Cross Couplings on DNA Conjugates Supported by Solid Support PEG-N⁺(Me)₃

The cationic solid support PEG-N⁺(Me)₃ (or DEAE sepharose) adjusted to 20 mL with glycerol:water 1:1) (200 µL, 0.00100 µmol) was washed with 3×1 mL H₂O in a 1 ml syringe equipped with a filter and then incubated for 15 min. with DNA-4-IODO (22.80 µL as a solution in water, 0.001 µmol) and 200 µL H₂O. The resin was washed with DMSO 4 times and transferred into a 2 ml glass vial containing a magnetic stirrer, using DMSO (Volume: 500 µL). 500 µl of the following solution A was added to this suspension under a positive pressure of argon. The vial was placed in a blue light photoreactor (470 nm) and irradiated for 60 min. at room temperature. (Solution A: 1-BOC-piperidine-4-carboxylic acid (22.93 mg, 0.100 mmol) was dissolved in a solution of Cs₂CO₃ (16.29 mg, 0.05 mmol) in water (250 µl) was added. The solution was shaken for 30 seconds and evaporated to dryness on a rotary evaporator. After evaporation the solid cesium salt of 1-BOC-piperidine-4-carboxylic acid (22.93 mg, 0.100 mmol) was dissolved in DMSO (Volume: 2000 µL) and added to a solution of NiCl₂(dme) (2.197 mg, 10 µmol), 4,4'-di-tert-butyl-2,2'-bipyridine (2.68 mg, 10 µmol) and Ir[dF(CF₃)ppy]₂(dtbbpy) PF₆ (2.244 mg, 2 µmol) in DMSO (Volume: 3000 µL) in a 20-mL microwave vial. The solution A was degassed by Argon bubbling.) Workup: The resin was transferred into a 1 mL syringe equipped with a filter, the solvent filtered and the resin washed 5 times with DMSO. The resin was incubated with 400 µL H₂O overnight and filtered into a 5 mL 3K Ultrafiltration device. Then 200 µL DNA elute solution (1.5 M NaCl, 50 mM phosphate buffer pH 8, 0.005% triton-X, 5% 4-Me-piperidine) was added to the resin, incubated for 30 min at 50° C. and filtered into the same Ultrafiltration device. The samples where then diluted to 5 mL with water, purified by ultrafiltration, recovered and evaporated to dryness. The residue was dissolved in 150 µL H₂O and analyzed by TOF LC-MS. Column: ACQUITY BEH OST C18 2.1×50 mm 1.7 um at 60° C.: Eluent A: water+10 mM TEA+200 mM HFIP Vial: 2:35 Gradient: 8-40% B in 2.7 min; 40-85% B in 0.95 min; 85-100% B in 0.05 min; 100% for 0.8 min Eluent B: 100% Methanol Flow: 0.6 mL/min. Rt=2.158, 6588.26 amu (M after deconvolution with Agilent MassHunter Qualitative Analysis 6.00)(Calc. 6588.548), interpreted as compatible with the structure of the final compound DNA-Boc-Pip.

Example 15

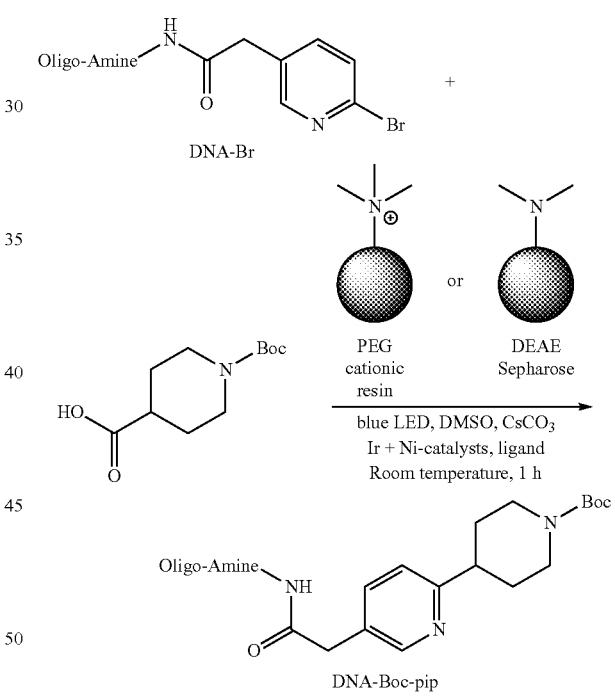

The oligonucleotide conjugate DNA-Br was prepared according to the method used for DNA-4-IODO.

The different solid supports were tested in the reaction conditions above for the conversion of DNA-Br into DNA-Boc-Pip and led to the conversions summarized in table 1 below:

TABLE 1

| Solid support | Percentage of added water (%) | Conversion into DNA-Boc-Pip (%) |
|---|---|---|
| PEG-N⁺(Me)₃ | 0 | 30 |
| DEAE sepharose | 0 | 0 |

TABLE 1-continued

| Solid support | Percentage of added water (%) | Conversion into DNA-Boc-Pip (%) |
|---|---|---|
| PEG-N$^+$(Me)$_3$ | 10 | 0 |
| PEG-N$^+$(Me)$_3$ | 25 | 0 |
| PEG-N$^+$(Me)$_3$ | 50 | 0 |

Example 16

Comparison of Different Cationic PEG Resins

This experiment aims to demonstrate that resins with different linkers and cationic groups can be used to effect a chemical transformation of oligonucleotides.

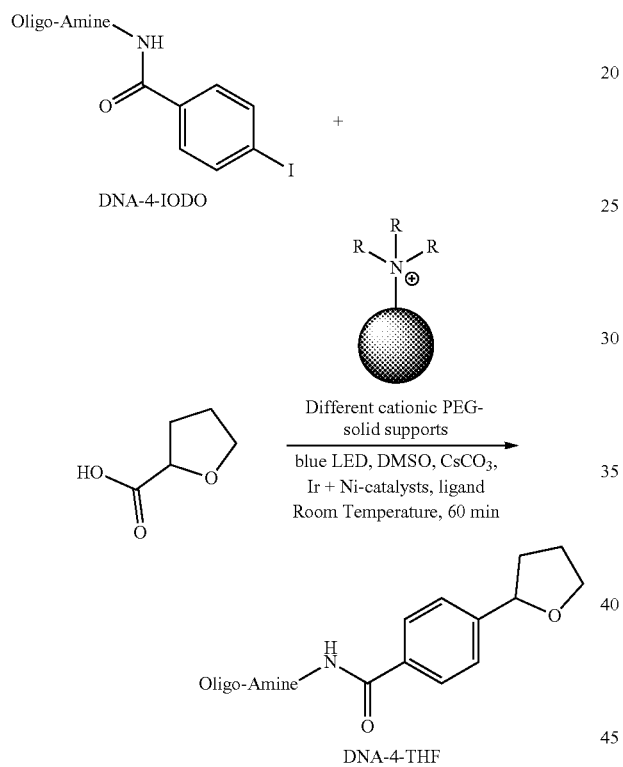

Equipment: 1 mL syringes with equipped with Filter insert, 5 mL glass vial, magnetic stirrer, photoreactor (2 W, 470 nm).

Standard Conditions for Photochemical Decarboxylative Cross Couplings on DNA Conjugates Supported by Solid Support PEG-N$^+$(Me)$_3$ PEG-N$^+$(Me)$_3$ (PEG-N$^+$(Me)$_3$ adjusted to 20 mL with glycerol:water 1:1) (200 µL, 0.00100 µmol) was washed with 3×1 mL H$_2$O in a 1 ml syringe equipped with a filter and then incubated for 15 min with DNA-4-IODO (6.52 µg, 0.001 µmol) as a solution in water and 200 uL H$_2$O. The resin was washed with DMSO 4 times and transferred into a 2 ml glass vial containing a magnetic stirrer, using DMSO (Volume: 500 µL). 500 µl of the following solution A was added to this suspension under air. The vial was placed in a photoreactor (470 nm) and irradiated for 60 min.

Solution A: tetrahydrofuran-2-carboxylic acid (9.57 µL, 0.100 mmol) was dissolved in MeOH (150 µL) and added to a solution of Cs$_2$CO$_3$ (16.29 mg, 0.05 mmol) in water (150 µl). The solution was shaken for 30 seconds and evaporated to dryness on a rotary evaporator. This Cs salt of tetrahydrofuran-2-carboxylic acid (9.57 µL, 0.100 mmol) was dissolved in DMSO (Volume: 2000 µL) and added to a solution of NiCl$_2$(dme) (2.197 mg, 10 µmol), 4,4'-di-tert-butyl-2,2'-bipyridine (2.68 mg, 10 µmol) and Ir[dF(CF$_3$)ppy]$_2$(dtbbpy)PF$_6$ (2.244 mg, 2 µmol) in DMSO (Volume: 3000 µL) in a 20 mL microwave vial. The solution was degassed by Argon bubbling. Workup: The resin was retransferred into a 1 mL filter syringe, the solvent filtered and the resin washed 5 times with DMSO. The resin was incubated 15 min at 50° C. with 100 µL H$_2$O and filtered. Then 100 µL DNA elute solution (1.5 M NaCl, 50 mM phosphate buffer pH 8, 0.005% triton-X, 5% 4-Me-piperidine) was added to the resin, incubated for 30 min at 50° C. and filtered into the same tube. The samples where purified by size exclusion chromatography and analyzed by TOF LC-MS.

TOF LC-MS: Column: ACQUITY BEH OST C18 2.1×50 mm 1.7 um at 60° C.: Eluent A: water+10 mM TEA+200 mM HFIP Gradient: 8-40% B in 2.7 min; 40-85% B in 0.95 min; 85-100% B in 0.05 min; 100% for 0.8 min Eluent B: 100% Methanol Flow: 0.6 mL/min. Rt: 1.938, 6460.14 amu (M after deconvolution with Agilent MassHunter Qualitative Analysis 6.00)(Calc. 6460.373), interpreted as compatible with the structure of the final compound DNA-4-THF.

The different solid supports tested led to the conversions under the standard conditions described above and are summarized in table 2 below:

TABLE 2

| Solid support | Observed conversion into DNA-4-THF (%) |
|---|---|
| PEG-N$^+$(Me)$_3$ | 93 |
| PEG-N$^+$(Me)$_2$Bn | 93 |
| PEG-N$^+$(Et)$_3$ | 92 |
| PEG-N$^+$(Bu)$_3$ | 90 |
| PEG-Bn-N$^+$(Me)$_3$ | 93 |
| PEG-Cyclohexane-N$^+$(Me)$_3$ | 93 |
| PEG-Napht-N$^+$(Me)$_3$ | 93 |
| Amino-PEG-N$^+$(Me)$_3$ | 92 |

Example 17

Comparison of Different Cationic PEG Resins on a Different Substrate

This experiment aims to demonstrate that resins with different linkers and cationic groups can be used to effect a chemical transformation of oligonucleotides.

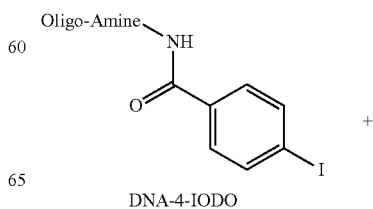

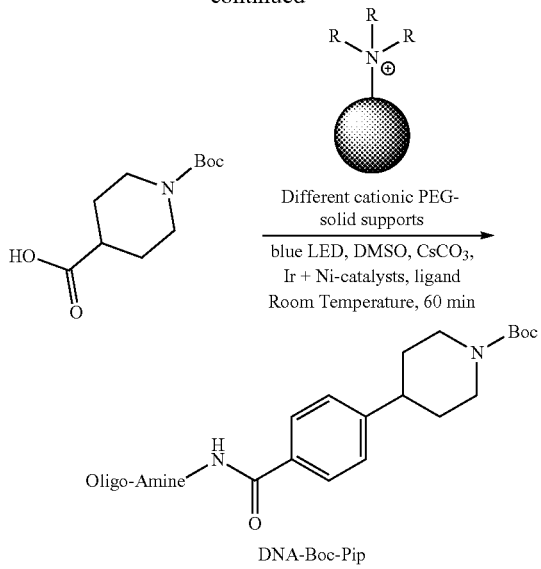

DNA-Boc-Pip

Equipment: 1 mL syringes with equipped with Filter insert, 5 mL glass vial, magnetic stirrer, photoreactor (2 W, 470 nm).

Standard Conditions for Photochemical Decarboxylative Cross Couplings on DNA Conjugates Supported by Solid Support PEG-N$^+$(Me)$_3$ PEG-N$^+$(Me)$_3$ (PEG-N$^+$(Me)$_3$ adjusted to 20 mL with glycerol:water 1:1) (200 µL, 0.00100 µmol), washed with 3×1 mL H$_2$O in a 1 ml syringe equipped with a filter and then incubated for 15 min. with DNA-4-IODO (6.52 µg, 0.001 µmol) as a solution in water and 200 uL H$_2$O. The resin was washed with DMSO 4 times and transferred into a 2 ml glass vial containing a magnetic stirrer, using DMSO (Volume: 500 µL). 500 µl of the following solution A was added to this suspension under air. The vial was placed in a photoreactor (470 nm) and irradiated for 60 min. Solution A: BOC-piperidine-4-carboxylic acid (22.93 mg, 0.100 mmol) was dissolved in MeOH (150 µL) and added to a solution of Cs$_2$CO$_3$ (16.29 mg, 0.05 mmol) in water (150 µl). The solution was shaked for 30 seconds and evaporated to dryness on a rotary evaporator. This Cs salt of BOC-piperidine-4-carboxylic acid (22.93 mg, 0.100 mmol) was dissolved in DMSO (Volume: 2000 µL) and added to a solution of NiCl$_2$(dme) (2.197 mg, 10 µmol), 4,4'-di-tert-butyl-2,2'-bipyridine (2.68 mg, 10 µmol) and Ir[dF(CF$_3$)ppy]$_2$(dtbbpy) PF$_6$ (2.244 mg, 2 µmol) in DMSO (Volume: 3000 µL) in a 20 mL microwave vial. The solution was degassed by Argon bubbling. Workup: The resin was retransferred into a 1 mL filter syringe, the solvent filtered and the resin washed 5 times with DMSO. The resin was incubated 15 min at 50° C. with 100 µL H$_2$O and filtered. Then 100 µL DNA elute solution (1.5 M NaCl, 50 mM phosphate buffer pH 8, 0.005% triton-X, 5% 4-Me-piperidine) was added to the resin, incubated for 30 min at 50° C. and filtered into the same tube. The samples where purified by size exclusion chromatography and analyzed by TOF LC-MS.

TOF LC-MS: Column: ACQUITY BEH OST C18 2.1×50 mm 1.7 um at 60° C.: Eluent A: water+10 mM TEA+200 mM HFIP Gradient: 8-40% B in 2.7 min; 40-85% B in 0.95 min; 85-100% B in 0.05 min; 100% for 0.8 min Eluent B: 100% Methanol Flow: 0.6 mL/min. Rt: 1.938, 6573.21 amu (M after deconvolution with Agilent MassHunter Qualitative Analysis 6.00)(Calc. 6573.533), interpreted as compatible with the structure of the final compound DNA-Boc-Pip.

The different solid supports were tested an led to the conversion of DNA-4-IODO into DNA-Boc-Pip summarized in table 3 below:

TABLE 3

| Solid support | Observed conversion into DNA-Boc-Pip (%) |
|---|---|
| PEG-N$^+$(Me)$_3$ | 45 |
| PEG-N$^+$(Me)$_2$Bn | 30 |
| PEG-N$^+$(Et)$_3$ | 30 |
| PEG-Bn-N$^+$(Me)$_3$ | 43 |
| PEG-Cyclohexane-N$^+$(Me)$_3$ | 45 |
| PEG-Napht-N$^+$(Me)$_3$ | 49 |
| Amino-PEG-N$^+$(Me)$_3$ | 38 |

Example 18

Experiment to Study the Effect of the Resin Counterion on the Conversion of a Chemical Transformation Equipment: 1 mL PALL Filter plate (AcroPrep™ Advance 96-Well Filter Plates for Aqueous Filtration PRODUCT ID 8019), magnetic stirrer, photoreactor equipped with lenses (Abon, 96×833 mW, 470 nm).

Resin Washing Procedure

In order to replace the counterion on the resin, the cationic resin PEG-N$^+$(Me)$_3$ was left to equilibrate with an aqueous solution of the sodium salt of the counterion to be introduced. For example 100 µL of a suspension of PEG-N$^+$(Me)$_3$ in water were filtered in a 1 mL PALL filtration plate and washed with 2×800 µL water. The resin was then incubated 30 min at 60° C. with 800 uL sodium iodide (NaI) 1.5 M in water. The suspension was filtered and washed with 800 µL of the same solution, followed by 2×800 µL H$_2$O. The resin was then incubated with 800 µL water and washed with 3×800 µL water.

This procedure was repeated to replace the bromide counterion with PF6$^-$ using a 0.3 M solution of sodium hexafluorophosphate (NaPF$_6$) in water.

Standard Conditions for Photochemical Decarboxylative Cross Couplings on DNA Conjugates Supported by Solid Support PEG-N$^+$(Me)$_3$ PEG-N$^+$(Me)$_3$ (PEG-N$^+$(Me)$_3$ adjusted to 20 mL with glycerol:water 1:1) (200 µL, 0.00100 µmol) was washed with 3×1 mL H$_2$O in a 1 ml syringe equipped with a filter and then incubated for 15 min with DNA-4-IODO (6.52 µg, 0.001 µmol) as a solution in water and 200 uL H$_2$O. The resin was washed with DMSO 4 times and transferred into a 2 ml glass vial containing a magnetic stirrer, using DMSO (Volume: 500 µL). 500 µl of the following solution A was added to this suspension under air. The vial was placed in a photoreactor (470 nm) and irradiated for 60 min. Solution A: BOC-piperidine-4-carboxylic acid (22.93 mg, 0.100 mmol) was dissolved in MeOH (150 µL) and added to a solution of Cs$_2$CO$_3$ (16.29 mg, 0.05 mmol) in water (150 µl). The solution was shaken for 30 seconds and evaporated to dryness on a rotary evaporator. This Cs salt of BOC-piperidine-4-carboxylic acid (22.93 mg, 0.100 mmol) was dissolved in DMSO (Volume: 2000 µL) and added to a solution of NiCl$_2$(dme) (2.197 mg, 10 µmol), 4,4'-di-tert-butyl-2,2'-bipyridine (2.68 mg, 10 µmol) and Ir[dF(CF$_3$)ppy]$_2$(dtbbpy) PF$_6$ (2.244 mg, 2 µmol) in DMSO (Volume: 3000 µL) in a 20 mL microwave vial. The solution was degassed by Argon bubbling. Workup: The resin was retransferred into a 1 mL filter syringe, the solvent filtered and the resin washed 5 times with DMSO. The resin was incubated 15 min at 50° C. with 100 μL H$_2$O and filtered. Then 100 μL DNA elute solution (1.5 M NaCl, 50 mM phosphate buffer pH 8, 0.005% triton-X, 5% 4-Me-piperidine) was added to the resin, incubated for 30 min at 50° C. and filtered into the same tube. The samples where purified by size exclusion chromatography and analyzed by TOF LC-MS.

TOF LC-MS: Column: ACQUITY BEH OST C18 2.1×50 mm 1.7 um at 60° C.: Eluent A: water+10 mM TEA+200 mM HFIP Gradient: 8-40% B in 2.7 min; 40-85% B in 0.95 min; 85-100% B in 0.05 min; 100% for 0.8 min Eluent B: 100% Methanol Flow: 0.6 mL/min. Rt: 1.938, 6573.22 amu (M after deconvolution with Agilent MassHunter Qualitative Analysis 6.00)(Calc. 6573.533), interpreted as compatible with the structure of the final compound DNA-Boc-Pip.

The different solid supports were tested under the standard conditions described above and led to the conversions summarized in table 4 below.

TABLE 4

| Solid support | Counterion | Observed conversion into DNA-Boc-Pip (%) |
| --- | --- | --- |
| PEG-N$^+$(Me)$_3$ | Br$^-$ | 30 |
| PEG-N$^+$(Me)$_2$Bn | I$^-$ | 6 |
| PEG-N$^+$(Et)$_3$ | PF$_6^-$ | 35 |

These results demonstrate that the amphiphilic PEG solid supports of the invention are useful to facilitate the transfer of important organic chemistry reactions to the elaboration of DNA-encoded libraries, thus increasing the boundaries of the chemical space that can be explored by this library generation technology. The results described herein demonstrate that it is possible to effect transformations that are challenging in the presence of oligonucleotides, such as those requiring formal carbanions, or the generation of reactive radicals. This has been achieved through adsorption of DNA onto the polymer matrix in a relatively lipophilic environment by means of cationic moieties, which protect the oligonucleotide chain leaving the nascent small molecule free to react at the periphery of the bead. Essentially, such solid-supported DNA chemistry methodologies enable the synthesis of next-generation DNA-encoded libraries.

The invention claimed is:

1. A solid support for use in non-aqueous DNA-conjugated molecule reactions, wherein the support comprises a solid body formed from a plurality of polyethylene glycol units, wherein the solid body includes at least one cationic moiety, wherein the cationic moiety includes a quaternary ammonium group or a guanidinium group, and wherein the cationic moiety is a compound according to Formula I:

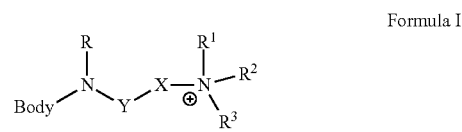

Formula I wherein:
Body is the solid support formed from a plurality of polyethylene glycol units;
R is hydrogen; C$_1$-C$_8$ alkyl optionally substituted by hydroxy, phenyl, C$_3$-C$_8$ cycloalkyl, 5 to 10 membered heterocyclic ring or —OC$_1$-C$_8$ alkyl; C$_3$-C$_8$ cycloalkyl; —C(O)C$_1$-C$_8$ alkyl; or a 5 to 10 membered heterocyclic ring;
X is X$_1$ or X$_2$, wherein
X$_1$ is a C$_1$-C$_{20}$ alkylene chain, wherein the chain is straight or branched and is optionally substituted by one or more substituents selected from halogen, —OH, C$_1$-C$_8$ alkoxy, nitro, cyano, —COOH, carbamoyl, —N(R$^4$)R$^5$, C$_3$-C$_6$ cycloalkyl, 3 to 7 membered heterocyclic ring, phenyl, 5 or 6 membered heteroaryl, or C$_1$-C$_4$ alkyl-phenyl;
X$_2$ is —Z—X$_1$—
wherein Z is selected from —(CH$_2$)$_a$—R$_x$—(CH$_2$)$_a$—NH—C(=O)—; —(CH$_2$)$_a$—CH((CH$_2$)$_a$—R$_{x1}$)NH—C(=O)—; —(CH$_2$)$_a$—(O)$_{0-1}$—R$_{x2}$—CH(R$_{x3}$)NH—C(=O)—; and —(CH$_2$)$_b$—(O)$_{0-1}$—(CH$_2$)$_b$—NH—C(=O)—;
a is an integer from 0 to 6;
b is an integer from 1 to 6;
R$_x$ is selected from phenyl; C$_3$-C$_8$ cycloalkylene; —C(H)$_{2-x}$((C$_1$-C$_6$alkyl)$_x$)-; naphthyl; and anthracyl, which phenyl, C$_3$-C$_8$ cycloalkylene, C$_1$-C$_6$alkyl, naphthyl or anthracyl are optionally substituted 1, 2, 3 or 4 times independently with C$_1$-C$_6$alkyl, C$_1$-C$_6$alkoxy, C$_1$-C$_6$ haloalkyl or halo;
R$_{x1}$ is selected from phenyl; C$_3$-C$_8$ cycloalkyl; naphthyl; and anthracyl,
which phenyl, C$_3$-C$_8$ cycloalkyl, naphthyl or anthracyl are optionally substituted 1, 2, 3 or 4 times independently with C$_1$-C$_6$alkyl, C$_1$-C$_6$alkoxy, C$_1$-C$_6$ haloalkyl or halo;
R$_{x2}$ is selected from phenyl; C$_3$-C$_8$ cycloalkylene; naphthyl; and anthracyl,
which phenyl, C$_3$-C$_8$ cycloalkylene, naphthyl or anthracyl are optionally substituted 1, 2, 3 or 4 times independently with C$_1$-C$_6$alkyl, C$_1$-C$_6$alkoxy, C$_1$-C$_6$ haloalkyl or halo;

$R_{x3}$ is selected from hydrogen; phenyl; and $C_3$-$C_6$cycloalkyl,
which phenyl or $C_3$-$C_6$cycloalkyl are optionally substituted 1, 2, 3 or 4 times independently with $C_1$-$C_6$alkyl; $C_1$-$C_6$alkoxy; $C_1$-$C_6$ haloalkyl or halo;

x is an integer from 0 to 2;
Y is C(O); and
$R^1$, $R^2$, $R^3$ are each independently selected from hydroxy; $C_1$-$C_8$ alkyl optionally substituted by hydroxy, phenyl, $C_3$-$C_8$ cycloalkyl, 5 to 10 membered heterocyclic ring or —O$C_1$-$C_8$ alkyl; $C_3$-$C_8$ cycloalkyl; —C(O)$C_1$-$C_8$ alkyl; or a 5 to 10 membered heterocyclic ring;

$R^4$ and $R^5$ are each independently selected from hydrogen; hydroxy; $C_1$-$C_8$ alkyl optionally substituted by hydroxy, phenyl, $C_3$-$C_8$ cycloalkyl, 5 to 10 membered heterocyclic ring or —O$C_1$-$C_8$ alkyl; $C_3$-$C_8$ cycloalkyl; —C(O)$C_1$-$C_8$ alkyl; or a 5 to 10 membered heterocyclic ring.

2. The solid support according to claim 1, wherein $R^1$, $R^2$, $R^3$, $R^4$ and $R^5$ are each independently selected from $C_1$-$C_8$ alkyl optionally substituted by phenyl or $C_3$-$C_8$ cycloalkyl; or $C_3$-$C_8$ cycloalkyl.

3. The solid support according to claim 1, wherein $X_1$ is a $C_1$-$C_{20}$ alkylene chain wherein the chain is straight or branched and is unsubstituted.

4. The solid support according to claim 3, wherein $X_1$ is a $C_1$-$C_{10}$ alkylene chain wherein the chain is straight and is unsubstituted.

5. The solid support according to claim 1, wherein R is H.

6. The solid support according to claim 1, wherein $R^1$, $R^2$ and $R^3$ are each independently a $C_1$-$C_6$ alkyl.

7. The solid support according to claim 6, wherein $R^1$, $R^2$ and $R^3$ are the same.

8. The solid support according to claim 7, wherein $R^1$, $R^2$ and $R^3$ are each methyl.

9. The solid support according to claim 1, wherein $R^4$ and $R^5$ are each independently selected from hydrogen and a $C_1$-$C_6$ alkyl.

10. The solid support according to claim 1, wherein the solid body is formed from a cross-linked polyethylene glycol polymer.

11. The solid support according to claim 1, wherein the solid body is formed from the NovaPEG resin of formula (IV)

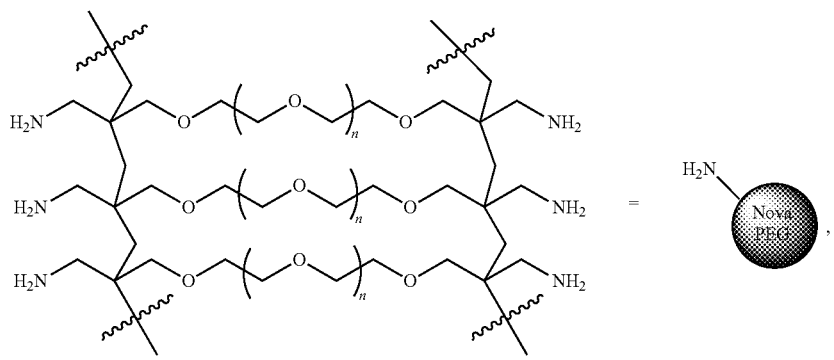

PEGA resin of formula (V)

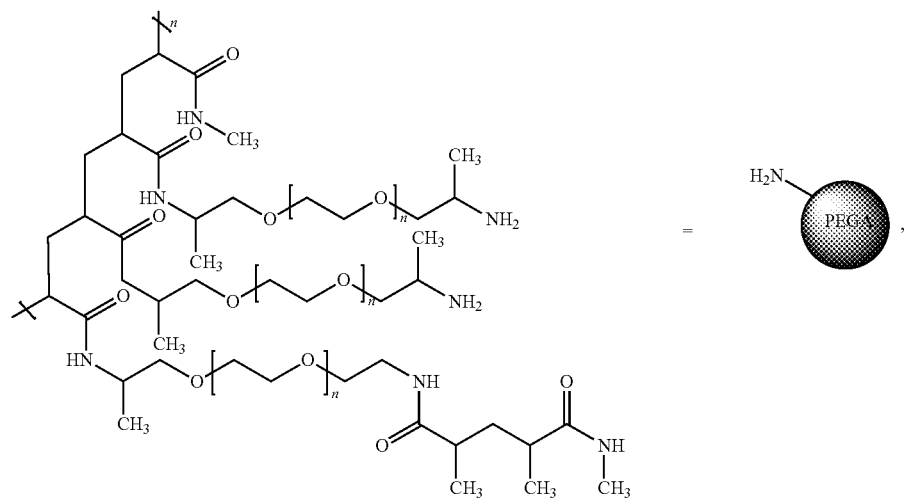

or the TentaGel resin of formula (VI).

12. The solid support according to claim 11, wherein the solid body is formed from the NovaPEG resin of formula (IV).

13. A method of reacting a DNA-conjugated compound using one or more non-aqueous solvents, wherein the method includes the steps of:
   i) adsorbing the DNA-conjugated compound onto a solid support as defined in claim 1; and
   ii) reacting the supported DNA-conjugated compound with a reagent in a non-aqueous solvent system.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
tacagctatg acttgcttag                                           20